(12) United States Patent
Weiss et al.

(10) Patent No.: US 8,143,220 B2
(45) Date of Patent: *Mar. 27, 2012

(54) DOSING REGIMENS FOR NEURAL STEM CELL PROLIFERATING AGENTS AND DIFFERENTIATING AGENTS FOR THE TREATMENT OF NEUROLOGICAL DISORDERS

(75) Inventors: Samuel Weiss, Calgary (CA); Christopher Gregg, Cambridge, MA (US)

(73) Assignee: Stem Cell Therapeutics Corp., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/687,302

(22) Filed: Mar. 16, 2007

(65) Prior Publication Data

US 2008/0039389 A1    Feb. 14, 2008

Related U.S. Application Data

(60) Provisional application No. 60/783,500, filed on Mar. 17, 2006, provisional application No. 60/789,132, filed on Apr. 5, 2006, provisional application No. 60/862,669, filed on Oct. 24, 2006.

(51) Int. Cl.
  *A61P 25/28* (2006.01)
  *A61K 38/24* (2006.01)
(52) U.S. Cl. ......... 514/17.7; 514/9.8; 514/10.3; 514/7.7
(58) Field of Classification Search .................... None
  See application file for complete search history.

(56) References Cited

U.S. PATENT DOCUMENTS

| | | |
|---|---|---|
| 4,703,008 A | 10/1987 | Lin |
| 4,767,628 A | 8/1988 | Hutchinson |
| 4,801,575 A | 1/1989 | Pardridge |
| 4,902,680 A | 2/1990 | Aroonsakul |
| 5,023,252 A | 6/1991 | Hseih |
| 5,128,242 A | 7/1992 | Arimura et al. |
| 5,198,542 A | 3/1993 | Onda et al. |
| 5,208,320 A | 5/1993 | Kitada et al. |
| 5,231,178 A | 7/1993 | Holtz et al. |
| 5,268,164 A | 12/1993 | Kozarich et al. |
| 5,326,860 A | 7/1994 | Onda et al. |
| 5,441,868 A | 8/1995 | Lin |
| 5,473,054 A | 12/1995 | Jameson et al. |
| 5,505,206 A | 4/1996 | Walloch |
| 5,506,107 A | 4/1996 | Cunningham et al. |
| 5,506,206 A | 4/1996 | Kozarich et al. |
| 5,521,069 A | 5/1996 | Onda et al. |
| 5,527,527 A | 6/1996 | Friden |
| 5,547,935 A | 8/1996 | Mullenbach et al. |
| 5,547,993 A | 8/1996 | Miki |
| 5,559,143 A | 9/1996 | McDonald et al. |
| 5,614,184 A | 3/1997 | Sytkowski et al. |
| 5,621,080 A | 4/1997 | Lin |
| 5,623,050 A | 4/1997 | Kitada et al. |
| 5,686,416 A | 11/1997 | Kozarich et al. |
| 5,723,115 A | 3/1998 | Serrero |
| 5,750,376 A | 5/1998 | Weiss et al. |
| 5,753,506 A | 5/1998 | Johe |
| 5,767,251 A | 6/1998 | Reddy et al. |
| 5,773,569 A | 6/1998 | Wrighton et al. |
| 5,795,790 A | 8/1998 | Schinstine et al. |
| 5,801,147 A | 9/1998 | Kitada et al. |
| 5,833,988 A | 11/1998 | Friden |
| 5,837,460 A | 11/1998 | Von Feldt et al. |
| 5,851,832 A | 12/1998 | Weiss et al. |
| 5,877,169 A | 3/1999 | Simpkins |
| 5,885,574 A | 3/1999 | Elliott |
| 5,955,346 A | 9/1999 | Wells et al. |
| 5,977,307 A | 11/1999 | Friden et al. |
| 5,980,885 A | 11/1999 | Weiss et al. |
| 6,015,555 A | 1/2000 | Friden |
| 6,017,533 A | 1/2000 | Moro et al. |
| 6,048,971 A | 4/2000 | Sytkowski et al. |
| 6,165,783 A | 12/2000 | Weiss et al. |
| 6,191,106 B1 | 2/2001 | Mullenbach et al. |
| 6,239,105 B1 | 5/2001 | Brewitt |
| 6,242,563 B1 | 6/2001 | Dong |
| 6,294,346 B1 | 9/2001 | Weiss et al. |
| 6,329,508 B1 | 12/2001 | Friden |
| 6,333,031 B1 | 12/2001 | Olsson et al. |
| 6,376,218 B1 | 4/2002 | Hsu et al. |
| 6,395,546 B1 | 5/2002 | Zobel et al. |
| 6,399,316 B1 | 6/2002 | Onda et al. |

(Continued)

FOREIGN PATENT DOCUMENTS

CA    2 175 992    5/1995

(Continued)

OTHER PUBLICATIONS

Belayev et al. Brain Res 1280: 117-123, 2009.*

(Continued)

*Primary Examiner* — Daniel E Kolker
*Assistant Examiner* — Aditi Dutt
(74) *Attorney, Agent, or Firm* — McKeon, Meunier, Carlin & Curfman, LLC

(57) ABSTRACT

Effective dosing regimens for neural stem cell proliferating and differentiating agents, kits comprising effective dosing regimens for neural stem cell proliferating and differentiating agents, and uses thereof are provided herein. Such kits and methods can be utilized acutely or chronically to treat a neurodegenerative disease or condition. Furthermore, the compositions and methods can be used continuously or intermittently in various dosing regimens.

2 Claims, 11 Drawing Sheets

U.S. PATENT DOCUMENTS

| | | | |
|---|---|---|---|
| 6,413,952 B1 | 7/2002 | Luengo et al. | |
| 6,429,186 B1 | 8/2002 | Fuh et al. | |
| 6,551,618 B2 | 4/2003 | Baird et al. | |
| 6,583,109 B1 | 6/2003 | Gallo et al. | |
| 6,618,698 B1 | 9/2003 | Beausoleil et al. | |
| 6,680,295 B1 | 1/2004 | Arimura | |
| 6,797,264 B1 | 9/2004 | Eriksson | |
| 6,812,027 B2 | 11/2004 | Goldman et al. | |
| 7,048,934 B2 | 5/2006 | Thompson et al. | |
| 7,132,287 B2 | 11/2006 | Rajan et al. | |
| 7,368,115 B2 | 5/2008 | Ohta et al. | |
| 7,393,830 B2 | 7/2008 | Shingo et al. | |
| 7,514,072 B1 | 4/2009 | Ehrenreich et al. | |
| 2002/0098178 A1 | 7/2002 | Brand | |
| 2003/0032181 A1 | 2/2003 | Weiss et al. | |
| 2003/0049838 A1* | 3/2003 | Thompson et al. | 435/368 |
| 2003/0054549 A1 | 3/2003 | Takebe et al. | |
| 2003/0054551 A1 | 3/2003 | Shingo et al. | |
| 2003/0054998 A1 | 3/2003 | Shingo et al. | |
| 2003/0060415 A1 | 3/2003 | Hung | |
| 2003/0130197 A1 | 7/2003 | Smith-Swintosky et al. | |
| 2004/0038888 A1 | 2/2004 | Mercer et al. | |
| 2004/0092448 A1 | 5/2004 | Ohta et al. | |
| 2004/0209000 A1 | 10/2004 | Curtiss et al. | |
| 2004/0209812 A1 | 10/2004 | Renzi et al. | |
| 2005/0009847 A1 | 1/2005 | Bertilsson et al. | |
| 2005/0245436 A1 | 11/2005 | Weiss et al. | |
| 2006/0089309 A1* | 4/2006 | Tucker | 514/15 |
| 2006/0121007 A1 | 6/2006 | Thompson et al. | |
| 2006/0148084 A1 | 7/2006 | Shingo et al. | |
| 2007/0098698 A1 | 5/2007 | Gregg et al. | |
| 2007/0111932 A1 | 5/2007 | Anderden | |
| 2007/0179092 A1 | 8/2007 | Ohta et al. | |
| 2008/0039389 A1 | 2/2008 | Weiss et al. | |
| 2008/0181873 A1 | 7/2008 | Shingo et al. | |
| 2008/0286234 A1 | 11/2008 | Eyink | |
| 2009/0325289 A1 | 12/2009 | Hatzfeld et al. | |
| 2010/0028361 A1 | 2/2010 | Smith et al. | |
| 2010/0047233 A1 | 2/2010 | Smith et al. | |
| 2011/0178009 A1 | 7/2011 | Weiss et al. | |

FOREIGN PATENT DOCUMENTS

| | | |
|---|---|---|
| CA | 2175992 | 5/1995 |
| CA | 2 353 553 | 6/2000 |
| CA | 2353553 A1 | 6/2000 |
| CA | 2 556 266 | 8/2005 |
| EP | 0467279 A3 | 1/1992 |
| WO | WO 90 05185 | 5/1990 |
| WO | WO 93 01275 | 1/1993 |
| WO | WO 94 09119 | 4/1994 |
| WO | WO 94 10292 | 5/1994 |
| WO | WO 96 09318 | 3/1996 |
| WO | W09615226 | 5/1996 |
| WO | WO 96/40231 | 12/1996 |
| WO | WO 97/48729 | 12/1997 |
| WO | 9805353 | 2/1998 |
| WO | WO 99 15191 | 4/1999 |
| WO | WO 99 21966 | 5/1999 |
| WO | WO 99 51272 | 10/1999 |
| WO | WO 00 05260 | 2/2000 |
| WO | WO 00 13650 | 3/2000 |
| WO | WO 00 30675 | 6/2000 |
| WO | WO 01 28574 | 4/2001 |
| WO | W00159074 | 8/2001 |
| WO | WO 03 018782 | 3/2003 |
| WO | WO 03 024472 | 3/2003 |
| WO | WO 03 35475 | 5/2003 |
| WO | WO 03/035475 A1 | 5/2003 |
| WO | WO 03 40310 | 5/2003 |
| WO | WO 03 092716 | 11/2003 |
| WO | 03103611 | 12/2003 |
| WO | W02004011021 | 2/2004 |
| WO | W02004011632 | 2/2004 |
| WO | W02004045592 | 6/2004 |
| WO | W02006037233 | 4/2006 |
| WO | WO 2007 106987 | 9/2007 |
| WO | WO2009057111 | 5/2009 |

OTHER PUBLICATIONS

Kolb B., et al., "Growth factor-stimulated generation of new cortical tissue and functional recovery after stroke damage to the motor cortex of rats" J Cerebral Blood Flow & Metabolism, Sep. 20, 2006, pp. 1-15.

Jin K. et al., "Alzheimer's disease drugs promote neurogenesis" Brain Research, Apr. 26, 2006, vol. 1085, No. 1, pp. 183-188.

Ohta S. et al., "Pituitary Adenylate Cyclase-Activating Polypeptide Regulates Forebrain Neural Stem Cells and Neurogenesis in Vitro and in Vivo" J Neuroscience Res., Nov. 1, 2006, vol. 84, No. 6, pp. 1177-1186.

Schanzer A. et al., "Direct Stimulation of Adult Neural Stem Cells in Vitro and Neurogenesis in Vivo by Vascular Endothelial Growth Factor" Brain Pathology, Jul. 2004, vol. 14, No. 3, pp. 237-248.

Scharfman H. et al., "Increased neurogenesis and the ectopic granule cells after intrahippocampal BDNF infusion in rats" Exp. Neuro., Apr. 2005, vol. 192, No. 2, pp. 348-356.

Tanaka R., "Potential of Use of Neural Stem Cells as Stroke as a Clinical Treatment" Juntendo Medical Journal, 2006, vol. 52, No. 1, pp. 2-10.

Al-Hader, A.A. et al. "Novel Expression of Functional Luteinizing Hormone/Chorionic Gonadotropin Receptors in Cultured Glial Cells from Neonatal Rat Brains" Biol. Reproduction, 1997, vol. 56, pp. 501-507.

Al-Hader, A.A. et al. "Neurons from Fetal Brains Contain Functional Luteinizing Hormone/Chorionic Gonadotropin Receptors" Biol. Reproduction, 1997, vol. 56, pp. 1071-1076.

Arlotta, P. et al. "Induction of Adult Neurogenesis" Ann. N.Y. Acad. of Sci. 2003, vol. 991, vol. 1, pp. 229-236.

Bithell, A. and Williams, B.P. "Neural stem cells and cell replacement therapy: making the right cells" Clin. Sci., 2005, vol. 108, pp. 13-22.

Curtis, M.A. et al. "Neurogenesis in the Diseased Adult Human Brain" Cell Cycle, 2003, vol. 2, No. 5, pp. 428-430.

Dulac, C. and Torello, T.T. "Molecular Detection of Pheromone Signals in Mammals: From Genes to Behaviour" 2003, vol. 4, No. 7, pp. 551-562, Nature Rev. Neurosc.

Fernandez-Pol, J.A. "Epidermal Growth Factor Receptor of A431 Cells" J. Biol. Chem., 1985, vol. 260, Apr. 25, 1985, pp. 5003-5011.

Fowler, C.D. et al. "The Effects of Social Environment on Adult Neurogenesis in the Female Prairie Vole" J. Neurobiol, 2002, vol. 51, pp. 115-128.

Frisèn, J. et al. "Central nervous system stem cells in the embryo and adult" Cell Mol. Life Sci., 1998, vol. 54, pp. 935-945.

Gage, F.H. "Mammalian Neural Stem Cells" Sci. 2000, vol. 287, pp. 1433-1438.

Huhtaniemi, I. et al. "Transgenic and knockout mouse models for the study of luteinizing hormone and luteinizing hormone receptor function" Mole. Cell. Endo., 2002, vol. 187, pp. 49-56.

Johnson, D.L. and Jolliffe, L.K. "Erythropoietin mimetic peptides and the future" Nephrol. Dial Transplant, 2000, vol. 15, pp. 1274-1277.

Karbanova, J. et al., "Neural Stem Cells Transplanted into Intact Brains as Neurospheres Form Solid Grafts Composed of Neurons, Astrocytes and Oligodendrocyte Precursors" Biomed Papers, 2004, vol. 148, No. 2, 217-220.

Kaushansky, K. "Hematopoietic Growth Factor Mimetics" Annals N.Y. Acad. Sci. 2001, vol. 938, pp. 131-138.

Kempermann, G. and Gage, F.H. "Experience-Dependent Regulation of Adult Hippocampal Neurogenesis: Effects of Long-Term Stimulation and Stimulus Withdrawal" Hippocampus, 1999, vol. 9, pp. 321-332.

Kiyokawa, Y. et al., "Modulatory role of testosterone in alarm pheromone release by male rates" Hormones and Behavior, 2004, vol. 45, p. 122-127.

Lei, Z.M. and Rao, Ch.V. "Neural Actions of Luteinizing Hormone and Human Chorionic Gonadotropin" Seminars in Reproductive Medicine, 2001, vol. 19, No. 1, pp. 103-109.

Luskin, M.B. "Rettricted Proliferation and Migration of Postnatally Generated Neurons Derived from the Forebrain Subventricular Zone" Neuron, 1993, vol. 11, pp. 173-189.

Ma, W. et al. "Role of the Adrenal Gland and Adrenal-Mediated Chemosignals in Suppression of Estrus in the House Mouse: The Lee-Boot Effect Revisited" Biol. Reproduction, 1998, vol. 59, pp. 1317-1320.

Menezes, J.R.L. et al. "The Division of Neuronal Progenitor Cells during Migration in the Neonatal Mammalian Forebrain" Mole. and Cell. Neuroscience, 1995, vol. 6, pp. 496-508.

Mode, A. et al. "The Human Growth Hormone (hGH) Antagonist $^{G120R}$ hGH Does Not Antagonize GH in the Rat, But Has Paradoxical Agonist Activity, Probably Via the Prolactin Receptor*" Endocrin., vol. 137, No. 2, pp. 447-454, 1996.

Moro, O. and Lerner, E.A. "Maxadilan, the Vasodilator from Sand Flies, Is a Specific Pituitary Adenylate Cyclase Activating Peptide Type I Receptor Agonist", J. Biol. Chem., 1997, vol. 272, No. 2, pp. 966-970.

Morrison, S. et al. "Regulatory Mechanisms in Stem Cell Biology" Cell, 1997, vol. 88, pp. 287-298.

Morshead, C.M. and Van Der Kooy, D. "Postmitotic Death is the Fate of Constitutively Proliferating Cells in the Subependymal Layer of the Adult Mouse Brain" J. Neuroscience, 1992, vol. 12, No. 1, pp. 249-256.

Nilsson, M. et al. "Enriched Environment Increases Neurogenesis in the Adult Rat Dentate Gyrus and Improves Spatial Memory" J. Neurobiol., 1999, vol. 39, vol. 4, pp. 569-578.

Ostenfeld, T. and Svendsen, C.N. "Recent Advances in Stem Cell Neurobiology" Adv. Tech. Stand Neurosurg., 2003, vol. 28, pp. 3-89.

Parker, M.A. et al. "Expression profile of an operationally-defined neural stem cell clone" Exp. Neuro., 2005, vol. 194, pp. 320-322.

Peretto, P. et al. "The subependymal layer in rodents: A site of structural plasticity and cell migration in the adult mammalian brain" Brain Res. Bull., 1999, vol. 49, No. 4, pp. 221-243.

Rao, M.S. "Multipotent and Restricted Precursors in the Central Nervous System" Anatomical Record (New Anat.) 1999, vol. 257, pp. 137-148.

Reynolds, B.A. and Weiss, S. "Clonal and Population Analyses Demonstrate That an EGF-Responsive Mammalian Embryonic CNS Precursor Is a Stem Cell" Developmental Biol., 1996, vol. 175, pp. 1-13.

Reynolds, B.A. and Weiss, S. "Generation and Neurons and Astrocytes from Isolated Cells of the Adult Mammalian Central Nervous System" Sci., 2005, vol. 255, No. 5052, pp. 1707-1710.

Reynolds, J.N. et al. "Ethanol modulation of GABA receptor-activated Cl⁻ currents in neurons of the chick, rate and mouse central nervous system" Eur. J. of Pharmaccology, 1992, vol. 224, pp. 173-181.

Rochefort, C. et al. "Enriched Odor Exposure Increases the Number of Newborn Neurons in the Adult Olfactory Bulb and Improves Odor Memory" J. Neuro., 2002, vol. 22, No. 7, pp. 2679-2689.

Rodriguez-Pena, A. "Oligodendrocyte Development and Thyroid Hormone" J. Neurobiol. 1999, vol. 40, pp. 497-512.

Shingo, T. et al. "Pregnancy-Stimulated Neurogensis in the Adult Female Forebrain Mediated by Prolactin" Sci., 2003, vol. 299, pp. 117-120.

Tanapat, P. et al. "Estrogen Stimulates a Transient Increase in the Number of New Neurons in the Dentate Gyrus of the Adult Female Rat" J Neuro., 1999, vol. 19, No. 14, pp. 5792-5801.

Weiss, S. et al. "Is there a neural stem cell in the mammalian forebrain" Trends Neurosci., 1996, vol. 19, pp. 387-393.

Wrighton, N.C. et al. "Small Peptides as Potent Mimetics of the Protein Hormone Erythropoietin", Sci., 1996, vol. 273, No. 5274, pp. 458-463.

Zhang F-P. et al. "Normal Prenatal but Arrested Postnatal Sexual Development of Luteinizing Hormone Receptor Knockout (LuRKO) Mice", Mol. Endo., 2005, vol. 15, No. 1, pp. 172-183.

Zhang J-X. et al. "Scent, social status, and reproductive condition in rat-like hamsters (*Cricetulus triton*)" Physiology & Behavior 2001, vol. 74, pp. 415-420.

Al-Hader et al., "Neurons from fetal rat brain contains functions luteinizing hormone/chorionic gonadotropin receptors," Biol. Reprod. 56:1071-1076 (1997).

Al-Hader et al., "Novel expression of functional luteinizing hormone/chorionic gonadotropin receptors in cultured glial cells from neonatal rat brains," Biol. Reprod. 56:501-507 (1997).

Arlotta et al., "Induction of Adult Neurogenesis," Ann. N.Y. Acad. Sci., 991(1):229-236 (2003).

Bayer, "Neuron production in the hippocampus and olfactory bulb of the adult rat brain: addition or replacement?" Ann. N.Y. Acad. Sci. 457:163-172 (1985).

Bernichtein et al., "S179D-human PRL, a pseudophosphorylated human PRL analog, is an agonist and not an antagonist," Endocrinology, 142(9):3950-3963 (2001).

Bithell & Williams, "Neural stem cells and cell replacement therapy: making the right cells," Clin. Sci., 108:13-22 (2005).

Brown et al., "Enriched environment and physical activity stimulate hippocampal but not olfactory bulb neurogenesis," Eur. J. Neurosci., 17(10):2042-2046 (2003).

Cerami et al., "Effects of Epoetin Alfa on the Central Nervous System," Seminars in Oncology, vol. 28, No. 2. Suppl 8, pp. 66-70 (2001).

Craig et al., "In vivo growth factor expansion of endogenous subependymal neural precursor cell populations in the adult mouse brain," J. Neurosci., 16(8):2649-2658 (1996).

Curtis et al., "Neurogenesis in the Diseased Adult Human Brain," Cell Cycle, 2(5):428-430 (2003).

Dicicco-Bloome et al., "The PACAP Ligand/Receptor System Regulates Cerebral Cortical Neurogenesis," Ann. N.Y. Acad. Sci., 865:274-289 (1998).

Fowler et al., "The effects of social environment on adult neurogenesis in the female prairie vole," J. Neurobiology, 51(2): 115-128 (2002).

Freed et al., "Survival of implanted fetal dopamine cells and neurologic improvement 12 to 46 months after transplantation for Parkinson's disease," N. Engl. J. Med., 327(22):1549-1555 (1992).

Frisén et al., "Central nervous system stem cells in the embryo and adult," Cell. Mol. Life Sci., 54(9):935-945 (1998).

Gage, "Mammalian neural stem cells," Science, 287:1433-1438 (2000).

Huhtaniemi et al., "Transgenic and knockout mouse models for the study of luteinizing hormone and luteinizing hormone receptor function," Mol. Cell. Endocrinol., 187(1-2):49-56 (2002).

Kaplan, "Neurogenesis in the 3-month-old rat visual cortex," J. Comp. Neurol., 195(2):323-338 (1981).

Karbanová et al., "Neural stem cells transplanted into intact brains as neurospheres form solid grafts composed of neurons, astrocytes and oligodendrocyte precursors," Biodmed. Papers, 148(2):217-220 (2004).

Kempermann & Gage, "Experience-dependent regulation of adult hippocampal neurogenesis: effects of long-term stimulation and stimulus withdrawal," Hippocampus, 9(3):321-332 (1999).

Kiyokawa et al., "Modulatory role of testosterone in alarm pheromone release by male rats," Horm. Behav., 45(2):122-127 (2004).

Lei & Rao, "Neural actions of luteinizing hormone and human chorionic gonadotropin," Seminars in Reprod. Med., 19(1):103-109 (2001).

Luskin, "Restricted proliferation and migration of postnatally generated neurons derived from the forebrain subventricular zone," Neuron, 11(1):173-189 (1993).

Ma et al., "Role of the adrenal gland and adrenal-mediated chemosignals in suppression of estrus in the house mouse: the Lee-Boot effect revisited," Biol. Reprod., 59(6):1317-1320 (1998).

Menezes et al., "The division of neuronal progenitor cells during migration in the neonatal mammalian forebrain," Mol. Cell. Neurosci., 6(6):496-508 (1995).

Morrison et al., "Regulatory mechanisms in stem cell biology," Cell, 88:287-298 (1997).

Morshead & Van Der Kooy, "Postmitotic death is the fate of constitutively proliferating cells in the subependymal layer of the adult mouse brain," J. Neurosci., 12(1):249-256 (1992).

Nilsson et al., "Enriched environment increased neurogenesis in the adult rat dentate gyms and improves spatial memory," J. Neurobiol., 39(4):569-578 (1999).

Ostenfeld & Svendsen, "Recent Advances in Stem Cell Neurobiology," Adv. Tech. Stand. Neurosurg., 28:3-89 (2003).

Park, "Transplantation of neural stem cells: cellular & gene therapy for hypoxic-ischemic brain injury," Yonsei Med. J., 41(6):825-835 (2000).

Parker et al., "Expression profile of an operationally-defined neural stem cell clone," Experimental Neurology, 194: 320-332 (2005).

Peretto et al., "The subependymal layer in rodents: a site of structural plasticity and cell migration in the adult mammalian brain," Brain Res. Bull., 49(4):221-243 (1999).

Perlow et al., "Brain grafts reduce motor abnormalities produced by destruction of nigrostriatal doparnine system," Science, 204(4393):643-647 (1979).

Potten & Loeffler, "Stem cells: attributes, cycles, spirals, pitfalls and uncertainties. Lessons for and from the crypt," Development, 110(4):1001-1020 (1990).

Rakic, "Limits of neurogenesis in primates," Science, 227(4690):1054-1056 (1985).

Rao, "Multipotent and restricted precursors in the central nervous system," Anat. Rec., 257(4):137-148 (1999).

Reynolds & Weiss, "Clonal and population analyses demonstrate that an EGF-responsive mammalian embryonic CNS precursor is a stem cell," Developmental Biology, 175:1-13 (1996).

Reynolds et al., "Ethanol modulation of GABA receptor-activated Cl$^-$ currents in neurons of the chick, rat and mouse central nervous system," Eur. J. Pharmacol., 224(2-3):173-181 (1992).

Reynolds & Weiss, "Generation of neurons and astrocytes from isolated cells of the adult mammalian central nervous system," Science, 255(5052):1707-1710 (1992).

Reitze et al., "Mitotically active cells that generate neurons and astrocytes are present in multiple regions of the adult mouse hippocampus," J. Comp. Neurol., 424(3):397-408 (2000).

Rochefort et al., "Enriched odor exposure increases the number of newborn neurons in the adult olfactory bulb and improves odor memory," J. Neurosci., 22:2679-2689 (2002).

Rodríguez-Peña, "Oligodendrocyte development and thyroid hormone," J. Neurobiol., 40(4):497-512 (1999).

Shingo et al. "Erythropoietin regulates the in vitro and in vivo production of neuronal progenitors by mammalian forebrain neural stem cells," J. Neurosci., 21(24):9733-9743 (2001).

Shingo et al., "Pregnancy-stimulated neurogenesis in the adult female forebrain mediated by prolactin," Science, 299:117-120 (2003).

Spencer et al., "Unilateral transplantation of human fetal mesencephalic tissue into the caudate nucleus of patients with Parkinson's disease," N. Engl. J. Med., 327(22):1541-1548 (1992).

Van Der Kooy & Weiss, "Why stem cells?" Science, 287(5457):1439-1441 (2000).

Widner et al., "Bilateral fetal mesencephalic grafting in two patients with parkinsonism induced by 1-methyl-4-phenyl-1,2,3,6-tetrahydropyridine (MPTP)," N. Engl. J. Med., 327(22):1556-1563 (1992).

Zhang et al., "Normal prenatal but arrested postnatal sexual development of luteinizing hormone receptor knockout (LuRKO) mice," Mol. Endocrinol., 15(1):172-183 (2001).

Al-Hader et al., "Fetal rat brains contain luteinizing hormone/human chorionic gonadotropin receptors," Early Pregnancy Biol. and Med. 3:323-9 (1997).

Ehrenreich et al., "Erythropoeitin therapy for acute stroke is both safe and beneficial," Mol. Med. 8(8):495-505 (2002).

Gritti et al., "Epidermal and fibroblast growth factors behave as mitogenic regulators for a single multipotent stem cell-like population from the subventricular region of the adult mouse forebrain," J. Neurosci. 19(9):3287-97 (1999).

Lei et al., "Novel expression of human chorionic gonadotropin/luteinizing hormone receptor gene in brain," Endocrinol. 132(5):2262-70 (1993).

Rao et al., "Human chorionic gonadotropin/luteinizing hormone receptor expression in the adult rat spinal cord," J. Neurosci. Letters 336:135-8 (2003).

Trinchard-Lugan et al., "Pharmacokinetics and pharmacodynamics of recombinant human chorionic gonadotropin in healthy male and female volunteers," Reproductive BioMed Online; www.rbmonline.com/Articl/280, Jan. 8, 2002.

English translation of RU 2003339 C1. Russian Federation Committee for Patents and Trademarks. Published Nov. 30, 1993.

Torner et al. "Prolactin Prevents Chronic Stress-Induced Decrease of Adult Hippocampal Neurogenesis and Promotes Neuronal Fate." *The Journal of Neuroscience*. 29(6): 1826-1833. Feb. 11, 2009.

Webber et al. "Gonadotropins and Alzheimer's Disease: the Link Between Estrogen Replacement Therapy and Neuroprotection." *Acta Neurobiol Exp.* 2004, 64: 113-118.

Aberg et al., "Peripheral Infusion of IGF-I Selectively Induces Neurogenesis in the Adult Rat Hippocampus," J. Neurosci. 20(8): 2896-2903 (2003).

Abramsky et al., "Suppressive Effect of Pregnancy on Ms and EAE," Prog. Clin. Biol. Res. 146:399-406 (1984).

Allen et al., "Sexual dimorphism and asymmetries in the gray-white composition of the human cerebrum," NeuroImage 18:880-894 (2003).

Anderson et al., "Insulin-like growth factor-1 and neurogenesis in the adult mammalian brain," Brain Res. Dev. Brain Res. 134(1-2):115-22 (2002).

Arimura et al., "PACAP functions as a neurotrophic factor," Ann. N.Y. Acad. Sci. 739:228-243 (1994).

Arimura et al., "Perspectives on pituitary adenylate cyclase activating polypeptide PACAP in the neuroendocrine, endocrine and nervous systems," Jap. J. Physiol. 48:301-331 (1998).

Arimura et al., "Tissue Distribution of PACAP as Determined by RIA: Highly Abundant in the Rat Brain Testes," Endocrinol. 129:2787-2789 (1991).

Arimura, "Pituitary adenylate cyclase activating polypeptide PACAP: Discovery and current status of research," Regulatory Peptides 37:287-303 (1992).

Armstrong et al., "Absence of fibroblast growth factor 2 promotes oligodendroglial repopulation of demyelinated white matter," J. Neurosci. 22(19):8574-8585 (2002).

Arnett et al., "TNFα promotes proliferation of oligodendrocyte progenitors and remyelination," Nature 4(11):1116-22 (2001).

Arsenijevic and Weiss, "Insulin-like Growth Factor-1 (IGF-I) Recruits a Distinct Population of Embryonic Neural Stem Cells," Mol. Biol. Cell 7(Supplement):1842 (1996).

Arsenijevic et al., "Insulin-like growth factor-I is necessary for neural stem cell proliferation and demonstrates distinct actions of epidermal growth factor and fibroblast growth factor-2," J. Neurosci., 21(18):7194-202 (2001).

Aston et al., "Transcriptional profiling reveals evidence for signaling and oligodendroglial abnormalities in the temporal cortex from patients with major depressive disorder," Mol. Psychiatry 10:309-322 (2005).

Bambakidis and Miller, "Transplantation of oligodendrocyte precursors and sonic hedgehog results in improved function and white matter sparing in the spinal cords of adult rats after contusion," J. Spine 4:16-26 (2004).

Banks et al., "Passage of pituitary adenylate cyclase activating polypeptide 1-27 and pituitary adenylate cyclase polypeptide 1-38 across the blood-brain barrier," J. Pharmacol. Exp. Ther. 267:690-6 (1993).

Bartzokis et al., "Heterogeneous age-related breakdown of white matter structural integrity: implications for cortical "disconnection," in aging and Alzheimer's disease," Neurobiol. Aging 25:843-851 (2004).

Bebo, Jr. and Dveksler, "Evidence that pregnancy specific glycoproteins regulate T-Cell function and inflammatory autoimmune disease during pregnancy," Curr. Drug Targets Inflamm. & Allergy 4:231-273 (2005).

Bebo, Jr., et al., "Low-dose estrogen therapy ameliorates experimental autoimmune encephalomyelitis in two different inbred mouse strains," J. Immunol. 166:2080-2089 (2001).

Brannvall et al., "Estrogen-receptor-dependent regulation of neural stem cell proliferation and differentiation," Mol. Cell. Neurosci. 21(3):512-20 (2002).

Brück and Stadelmann, "The spectrum of multiple sclerosis: new lessons from pathology," Curr. Opin. Neurol. 18:221-224 (2005).

Buckner, "Memory and executive function in aging and AD: multiple factors that cause decline and reserve factors that compensate," Neuron 44:195-208 (2004).

Camarillo et al., "Prolactin receptor expression in the epithelia and stroma of the rat mammary gland," J. Endocrinol. 171:85-95 (2001).

Cao et al., "Functional recovery in traumatic spinal cord injury after transplantation of multineurotrophin-expressing glial-restricted precursor cells," J. Neurosci. 25(30):6947-6957 (2005).

Carey et al., "Pituitary Adenylate Cyclase Activating Polypeptide Antimitogenic Signaling in Cerebral Cortical Progenitors is Regulated by p57Kip2-dependent CDK2 activity," J. Neurosci. 22(5):1583-91 (2002).

Cerghet et al., "Proliferation and death of oligodendrocytes and myelin proteins are differentially regulated in male and female rodents," J. Neurosci. 26(5):1439-1447 (2006).

Chikanza, "Prolactin and neuroimmunomodulation: in vitro and in vivo observations" Ann. N. Y. Acad. Sci. 876:119-130 (1999).

Chojnacki and Weiss, "Isolation of a novel platelet-derived growth factor-responsive precursor from the embryonic ventral forebrain," J. Neurosci. 24:10888-10899 (2004).

Christophe, "Type I Receptors for PACAP (a neuropeptide even more important than VIP?)," Biochim. Biophys. Acta 1154:183-99 (1993).

Confavreux et al., "Rate of pregnancy-related relapse in multiple sclerosis," N. Engl. J. Med. 339(5):285-91 (1998).

Cunningham et al., "High-resolution epitope mapping of hGH-receptor interactions by alanine-scanning mutagenesis," Science 244(4908):1081-5 (1989a).

Cunningham et al., "Receptor and antibody epitopes in human growth hormone identified by homolog-scanning mutagenesis," Science 243(4896):1330-1336 (1989b).

Dawson et al., "NG2-expressing glial progenitor cells an abundant and widespread population of cycling cells in the adult rat CNS," Mol. Cell. Neurosci. 24:476-488 (2003).

DeVito et al., "Prolactin induced expression of interleukin-1 alpha, tumor necrosis factor alpha, and transforming growth factor-alpha in cultured astrocytes," J. Cell Biochem. 57:290-298 (1995).

Dong and Greenough, "Plasticity of nonneuronal brain tissue: roles in developmental disorders," Ment. Retard. Dev. Disabil. Res. Rev. 10:85-90 (2004).

Draca and Levic, "The possible role of prolactin in the immunopathogenesis of multiple sclerosis," Med. Hypotheses 47:89-92 (1996).

Dubey et al., "Differential penetration of three anterior pituitary peptide hormones into the cerebrospinal fluid of rhesus monkeys," Life Sci. 32(16):1817-1863 (1983).

Faulkner et al., "Human embryonic stem cell-derived oligodendrocyte progenitors for the treatment of spinal cord injury," Transpl. Immunol. 15:131-142 (2005).

Ferro and Madureira, "Age-related white matter changes and cognitive impairment," Neurol. Sci. 203-204:221-225 (2002).

Fields, "Myelination: an overlooked mechanism of synaptic plasticity?," Neuroscientist 11(6):528-531 (2005).

Fleming and Walsh, "Neuropsychology of maternal behavior in the rat: c-fos expression during mother-litter interactions," Psychoneuroendocrinology 19(5-7):429-443 (1994).

Freeman et al., "Prolactin: structure, function and regulation of secretion," Physiol. Rev. 80: 1523-1631 (2000).

Gage et al., "Isolation, characterization, and use of stem cells from the CNS," Annu. Rev. Neurosci. 18:159-92 (1995).

Gage et al., "Survival and differentiation of adult neuronal progenitor cells transplanted to the adult brain," PNAS 92(25):11879-83 (1995).

Gatewood et al., "Motherhood mitigates aging-related decrements in learning and memory and positively affects brain aging in the rat," Brain Res. Bull. 66:91-98 (2005).

Gensert and Goldman, "In vivo characterization of endogenous proliferating cells in adult rat subcortical white matter," GLIA 17:39-51 (1996).

Gensert and Goldman, "Endogenous progenitors remyelinate demyelinated axons in the adult CNS," Neuron 19:197-203 (1997).

Goeddel et al., "Direct expression in *Escherichia coli* of a DNA sequence coding for human growth hormone," Nature 281(5732):544-548 (1979).

Goffin et al., "Sequence-Function Relationships within the Expanding Family of Prolactin, Growth Hormone, Placental Lactogen, and Related Proteins in Mammals," Endocrine Reviews 17:385-410 (2007).

Gray et al., "Periplasmic production of correctly processed human growth hormone in *Escherichia coli*: natural and bacterial signal sequences are interchangeable," Gene 39(2-3):247-254 (1985).

Gur et al., "Sex differences in brain gray and white matter in healthy young adults: correlations with cognitive performance," J. Neurosci. 19(10):4065-4072 (1999).

Hack et al., "Neuronal fate determinants of adult olfactory bulb neurogenesis," Nat. Neurosci. 8(7):865-872 (2005).

Haier et al., "The neuroanatomy of general intelligence: sex matters," Neuroimage 25:320-327 (2005).

Hansel et al., "Regulation of Olfactory Neurogenesis by Amidated Neuropeptides," J. Neurosci. Res. 66:1-7 (2001).

Hashimoto et al., "Altered Psychomotor Behaviors in Mice Lacking Pituitary Adenylate Cyclase-Activating Polypeptide (PACAP)," PNAS 98:(23)13355-13360 (2001).

Hashimoto et al., "Molecular Cloning and Tissue Distribution of a Receptor for Pituitary Adenylate Cyclase Activating Polypeptide," Neuron 11:333-342 (1993).

Hirose et al., "Gene expression of PACAP and its receptors in the ES cell-derived neuronal stem cells," Japanese J. Pharmacol. 88:143 (Supplement 1) (2002).

Inzitari, "Leukoaraiosis: an independent risk factor for stroke?," Stroke 34:2067-2071 (2003).

Ito et al., "Estrogen treatment down-regulates TNF a production and reduces the severity of experimental autoimmune encephalomyelitis in cytokine knockout mice," J. Immunol. 167:542-552 (2001).

Johnson et al., "Evaluating the Role of the Hormone Prolactin in Neuroinflammation and repair associated with exerimental autoimmune encephalomyelitis," EndMS Research Conference, Banff, Alberta Canada, Dec. 10-13, 2007.

Jokinen et al., "Medial temporal lobe atrophy and memory deficits in elderly stroke patients," Eur. J. Neurol. 11:825-832 (2004).

Kandel et al. (eds.), "Principles of Neural Science," 3d Ed., p. 981, Elsevier Science Publishing Co., New York (1991).

Karimi-Abdolrezaee et al., "Delayed transplantation of adult neural precursor cells promotes remyelination and functional neurological recovery after spinal cord injury," J. Neurosci. 26(13):3377-3389 (2006).

Keirstead et al., "Human embryonic stem cell-derived oligodendrocyte progenitor cell transplants remyelinate and restore locomotion after spinal cord injury," J. Neurosci. 25(19):4694-4075 (2005).

Kieseier et al., "Multiple sclerosis-novel insights and new therapeutic strategies," Curr. Opin. Neurol. 18:211-220 (2005).

Kim and Juraska, "Sex differences in the development of axon number in the splenium of the rat corpus callosum from postnatal day 15 through 60," Brain Res. Dev. Brain Res. 102:77 (1997).

Kim et al., "Estriol ameliorates autoimmune demyelinating disease: implications for multiple sclerosis," Neurology 52:1230-1238 (1999).

Kimura et al., "A Novel Peptide Which Stimulates Adenylate Cyclase: Molecular Cloning and Characterization of the Ovine and Human cDNAs," Biochem. Biophys. Res. Comm. 166:81-89 (1990).

Kinsley et al., "Motherhood improves learning and memory," Nature 402:137-138 (1999).

Kolb et al., "Nerve growth factor treatment prevents dendritic atrophy and promotes recovery of function after cortical injury," Neuroscience 76(4): 1139-1151 (1997).

Konishi et al., "Tropic effect of erythropoietin and other hematopoietic facotrs on central cholinergic neurons in vitro and in vivo," Brain Research 609:29-35 (1993).

Kovacs et al., "Olfactory Bulb in Multiple System Atrophy," Movement Disorder 18(8):938-942, (2003).

Lambert et al., "Pup exposure differentially enhances foraging ability in primiparous and nulliparous rats," Physiol. Behav. 84:799-806 (2005).

Learish et al., "Intraventricular transplantation of oligodendrocyte progenitors into a fetal myelin mutant results in widespread formation of myelin," Ann. Neurol. 46:716-722 (1999).

Lee et al., "Pituitary Adenylyl Cyclase-Activating Polypeptide Stimuiates DNA Synthesis but Delays Maturation of Oligodendrocyte Progenitors," J. Neurosci. 21(11):3849-3859 (2001).

Lee et al., "Effects of glial transplantation on functional recovery following acute spinal cord injury," J. Neurotrauma 22(5):575-589 (2005).

Lelievre et al., "Cross-talk between PACAP and sonic hedgehog (SHH) pathways in neural stem cells, cerebellar granular progenitor cells and oligodendrocyte progenitors to control cell fate and proliferation," Regulatory Peptides 115(1):50 (2003).

Lelievre et al., "Fibroblast growth factor-2 converts PACAP growth action on embryonic hindbrain precursors from stimulation to inhibition," J. Neurosci. Res. 67(5):566-573 (2002).

Lelievre et al., "Interactive of PACAP with sonic Hedgehog on neural stem cell and oligodendrocyte progenitor proliferation," J. Neurochem. 85:66 (Supplement 1) (2003).

Levine et al., "The oligodendrocyte precursor cell in health and disease," Trends Neurosci. 24(1):39-47 (2001).

Levison et al., "Cycling cells in the adult rat neocortex preferentially generate oligodendroglia," J. Neurosci. Res. 57:435-466 (1999).

Lim et al., "Noggin antagonizes BMP signaling to create a niche for adult neurogenesis," Neuron 28:713-726 (2000).

Lindholm et al., "Developmental Regulation of Pituitary Adenylate Cyclase Activating Polypeptide (PACAP) and its Receptor 1 in Rat Brain: Function of PACAP as a Neurotrophic Factor," Ann. N.Y. Acad. Sci. 865:189-196 (1998).

Livnah et al., "Functional mimicry of a protein hormone by a peptide agonist: the EPO receptor complex at 2.8 Å," Science 273(5274):464-471 (1996).

Lledo et al., "Adult neurogenesis and functional plasticity in neuronal circuits," Nat. Rev. Neurosci. 7:179-193 (2006).

Lobie et al., "Growth hormone, insulin-like growth factor I and the CNS: localization, function and mechanism of action," Growth Hormone & IGF Research (Supp. B):S51-S56 (2000).

Love et al., "Maternal experience produces long-lasting behavioral modification in the rat," Behav. Neurosci. 119(4):1084-1096 (2005).

Lowman et al., "Mutational analysis and protein engineering of receptor-binding determinants in human placental lactogen," J. Biol. Chem. 266:10982-10988 (1991).

Lu et al., "Pituitary Adenylate Cyclase-Activating Polypeptide is an Autocrine Inhibitor of Mitosis in cultured Cortical Precursor Cells," PNAS 94:3357-3362 (1997).

Lubetzki et al., "Promoting repair in multiple sclerosis: problems and prospects," Curr. Opin. Neurol. 18:237-244 (2005).

Lyoo et al., "White matter hyperintensities on magnetic resonance imaging of the brain in children with psychiatric disorders," Compr Psychiatry 43(5):361-368 (2002).

Mack et al., "Sex differences in the distribution of axon types within the genu of the rat corpus callosum," Brain Res 697:152-156 (1995).

Menn et al., "Origin of oligodendrocytes in the subventricular zone of the adult brain," J. Neurosci. 26(30):7907-7918 (2006).

Misra et al, "Drug delivery to the central nervous system: a review," J. Pharm. Pharmaceut. Sci. 6(2): 252-73 (2003).

Miyata et al., "Isolation of a Novel 38 Residue-Hypothalamic Polypeptide which Stimulates Adenylate Cyclase in Pituitary Cells," Biochem. Bophys. Res. Comm. 164:567-574 (1989).

Moderscheim et al., "Prolactin is Involved in Glial Responses Following a Focal Injury to the Juvenile Rat Brain," Neurosci. 145: 963-973 (2007).

Moore et al., "Cerebral white matter lesions in bipolar affective disorder: relationship to outcome," Br. J. Psychiatry 178:172-176 (2001).

Mori, "Impact of subcortical ischemic lesions on behavior and cognition," Ann. N. Y. Acad. Sci. 977:141-148 (2002).

Mulloy et al., "Absorption or orally administered bovine prolactin by neonatal rats," Biol. Neonate 36(3-4):148-53 (1979).

Nait-Oumesmar et al., "Progenitor cells of the adult mouse subventricular zone proliferate, migrate and differentiate into oligodendrocytes after demyelination," Eur. J. Neurosci. 11:4357-4366 (1999).

Neumann, "Alterations in behavioral and neuroendocrine stress coping strategies in pregnant parturient and lactating rats," Prog. Brain Res. 133:143-152 (2001).

Nicot et al., "Regulation of Neuroblast Mitosis is Determined by PACAP Receptor Isoform Expression," PNAS 98:(8)4758-4763 (2001).

Nuñez et al., "Myelination in the splenium of the corpus callosum in adult male and female rats," Dev. Brain Res. 120:87-90 (2000).

Nyberg, "Aging effects on growth hormone receptor binding in the brain," Exp. Gerontol. 32:521-528 (1997).

Nyberg, "Growth hormone in the brain: characteristics of specific brain targets for the hormone and their functional significance," Front. Neuroendocrinol. 21:330-348 (2000).

Ormandy et al., "Null mutation of the prolactin receptor gene produces multiple reproductive defects in the mouse," Genes Dev. 11:167-178 (1997).

Otto et al., "Altered Emotional Behavior in PACAP-type-I-receptor-deficient Mice," Brain Res. Mol. Brain Res. 91(1-2):78-84 (2001).

Patil, "The effect of Human Chorionic Gonadotropin (HCG) on Restoration of Physiological Continuity of the Spinal Cord. A Preliminary Report," Int. Surg. 75:54-57 (1990).

Patil, "The Study of the Effect of Human Chorionic Gonadotrophic (HCG) Hormone on the Survival of Adrenal Medulla Transplant in Brain. Preliminary Study," Acta Neurochirurgica 87:76-8 (1987).

Patil and Nagaraj, "The Effect of Human Chorionic Gonadotropin (HCG) on Functional Recovery of Spinal Cord Sectioned Rats*," Acta Neurochirurgica 69:205-18 (1983).

Patil and Nagaraj, Letter to the Editor, Neurosurgery 12(5):593-4 (1983).

Pesce et al., "Pituitary adenylate cyclass-activating polypeptide (PACAP) stimulates adenylate cyclase and promotes proliferation of mouse primordial germ cells," Development 122(1):215-221 (1996).

Peters and Sethares, "Oligodendrocytes, their progenitors and other neuroglial cells in the aging primate cerebral cortex," Cereb. Cortex 14:995-1007 (2004).

Peters et al., "Effects of aging on the neuroglial cells and pericytes within area 17 of the rhesus monkey cerebral cortex," Anat. Rec. 229:384-398 (1991).

Peters, "The effects of normal aging on myelin and nerve fibers: a review" J. Neurocytol. 31:581-593 (2002).

Phelps et al., "Stimulatory effect of human, but not bovine, growth hormone expression on numbers of tuberoinfundibular dopaminergic neurons in transgenic mice," Endocrinology 138(7):2849-2855 (1997).

Phelps et al., "Pituitary hormones as neurotrophic signals: Update on hypothalamic differentiation in genetic models of altered feedback," Proc. Soc. Exp. Biol. Med. 222(1):39-58 (1999).

Picard-Riera et al., "Experimental autoimmune encephalomyelitis mobilizes neural progenitors from the subventricular zone to undergo oligodendrogenesis in adult mice," PNAS 99(20):13211-13216 (2002).

Pluchino et al, "Injection of adult neurospheres induces recovery in a chronic model of multiple sclerosis," Nature 422(6933):688-94 (2003).

Polito and Reynolds, "NG2 expressing cells as oligodendrocyte progenitors in the normal and demyelinated adult central nervous system," Anat. 207:707-716 (2005).

Rawlings, "At the Cutting Edge PACAP, PACAP Receptors, and Intracellular Signalling," Mol. Cell. Endocrinol. 191:C5-C9 (1994).

Rostene et al., "VIP and PAGAP via G-Protein coupled receptors are potent inducers of mouse embryonic stem cell neuronal differentiation," Regulatory Peptides 115(1):55 (2003).

Scheepens et al., "Growth Hormone as a Neuronal Rescue Factor During Recovery from CNS Injury," Neurosci. 104(3):677-687 (2001).

Schlessinger et al., "Crystal structure of a ternary FGF-FGFR-heparin complex reveals a dual role for heparin in FGFR binding and dimerization," Mol. Cell 6:743-50 (2000).

Schradin and Anzenberger, "Prolactin, the Hormone of Paternity," News Physiol. Sci. 14:223-231 (1999).

Scolding and Franklin, "Remyelination in demyelinating disease," Baillieres Clin. Neurol. 6:525-548 (1997).

Shimazaki et al., "The ciliary neurotrophic factodleukemia inhibitory factor/gp130 receptor complex operates in the maintenance of mammalian forebrain neural stem cells," J. Neurosci. 21(19):7642-7653 (2001).

Shingo et al., Supporting Online Material pp. 1-10, "Pregnancy-Stimulated Neurogenesis in the Adult Female Forebrain Mediated by Prolactin" Science 299:117-20 (2003).

Shioda et al., "Pleiotropic functions of PACAP in the CNS. Neuroprotection and neurodevelopment," Ann. NY Acad. Sci. 1070:550-60 (2006).

Sicotte et al., "Treatment of multiple sclerosis with the pregnancy hormone estriol," Ann. Neurol. 52:421-428 (2002).

Silverstone et al., "Deep white matter hyperintensities in patients with bipolar depression, unipolar depression and age-matched control subjects," Bipolar Disord. 5:53-57 (2003).

Sirevaag and Greenough, "Differential rearing effects on rat visual cortex synapses. III. Neuronal and glial nuclei, boutons, dendrites and capillaries," Brain Res. 424:320-322 (1987).

Sorokan et al., "Erythropoietin mediates increased neurogenesis by embryonic CNS stem cells following a modest hypoxic insult," Soc. Neurosci. Abstracts, 23(1/2):320 (1997).

Stangel and Hartung, "Remyelinating strategies for the treatment of multiple sclerosis," Prog. Neurobiol. 68:361-376 (2002).

Stevens et al., "Adenosine: a neuron-glial transmitter promoting myelination in the CNS in response to action potentials," Neuron 36:855-868 (2002).

Studer et al., "Enhanced proliferation, survival, and dopaminergic differentiation of CNS precursors in lowered oxygen," J. Neurosci. 20(19):7377-7383 (2000).

Sturrock, "Myelination of the mouse corpus callosum," Neuropathol. Appl. Neurobiol. 6:415-420 (1980).

Szeligo and Leblond, "Response of the three main types of glial cells of cortex and corpus callosum in rats handled during suckling or exposed to enriched, control and impoverished environments following weaning," J. Comp. Neurol. 172:247-264 (1977).

Tang et al., "Long-term culture of purified postnatal oligodendrocyte precursor cells. Evidence for an intrinsic maturation program that plays out over months," J. Cell Biol. 148:971-984 (2000).

Tauber et al., "Myelination in rabbit optic nerves is accelerated by artificial eye opening," Neurosci. Lett. 16:235-238 (1980).

The American Heritage Dictionary of the English Language 4th Ed., Dictionary.com/neural (2000).

Totoiu and Keirstead, "Spinal cord injury is accompanied by chronic progressive demyelination," J. Comp. Neurol. 486:373-383 (2005).

Tropepe et al., "Transforming growth factor-alpha null and senescent mice show decreased neural progenitor cell proliferation in the forebrain subependyma," J. Neurosci. 17: 7850-7859 (1997).

Van Dam et al, "Growth Hormone, insulin-like growth factor I and cognitive function in adults," Growth Horm IGF Res. 10(Supp B):S69-73 (2000).

Van Walderveen et al., "Magnetic resonance evaluation of disease activity during pregnancy in multiple sclerosis," Neurology 44:327-329 (1994).

Vaudry et al., "Neurotrophic activity of pituitary adenylate cyclase-activating polypeptide on rate cerebellar cortex during development," PNAS 96(16):9415-9420 (1999).

Vaudry et al., "Pituitary Adenylate Cyclase-Activating Polypeptide and Its Receptors from Structure to Functions," Pharmacol. Rev. 52:269-324 (2000).

Voskuhl, "Hormone-based therapies in MS," Int. MS J. 10:60-66 (2003).

Walker et al., "Mother to infant or infant to mother? Reciprocal regulation of responsiveness to stress in rodents and the implications for humans," J. Psychiatry Neurosci. 29(5):364-382 (2004).

Wardlaw et al., "Is diffusion imaging appearance an independent predictor of outcome after ischemic stroke?," Neurology 59:1381-1387 (2002).

Waschek, "Multiple actions of pituitary adenylyl cyclase activating peptide in nervous system development and regeneration," Develop. Neurosci. 24:14-23 (2002).

Waschek, "VIP and PACAP Receptor-mediated Actions on Cell Proliferation and Survival," Ann. N.Y. Acad. Sci. 805:290-300 (1996).

Weetman, "The immunology of pregnancy," Thyroid 9(7):643-646 (1999).

Whittemore et al., "Mitogen and substrate differentially affect the lineage restriction of adult rat subventricular zone neural precursor cell populations," Exp. Cell Res. 252:75-95 (1999).

Wu et al., "Expression of QKI proteins and MAP1B identifies actively myelinating oligodendrocytes in adult rat brain," Mol. Cell. Neurosci. 17:292-302 (2001).

Yuhara et al., "PACAP has a Neurotrophic Effect on Cultured Basal Forebrain Cholinergic Neurons from Adult Rats," Brain Res. Dev. Brain Res. 131(1):41-5 (2001).

Ehrenreich et al., "Recombinant Human Erythropoietin in the Treatment of Acute Ischemic Stroke," Stroke. 2009; 40: 00-00.

Minnerup et al., "The Efficacy of Erythropoietin and Its Analogues in Animal Stroke Models: A Meta-Analysis," American Heart Association, Inc. pp. 3113-3120. 2009.

Choi, H.K. and Waxman, D. "Growth Hormone, but Not Prolactin, Maintains Low-Level Activation of STAT5a and STAT5b in Female Rat Liver." Endocrinology 140: 5126-5135, 1999.

Chojnacki, A. and Weiss, S., "Expression and putative function of MASH1 and MASH2 in EGF-responsive forebrain neural stem cells." Society for Neuroscience, Presentation No. 600.14. Nov. 8, 2000.

Faden, A. et al. "Treatment of experimental stroke: Comparison of naloxone and thyrotropin releasing hormone." Neurology; 32: 1083-7. 1982.

Markianos, M. et al. "Serum and Cerebrospinal Fluid Prolactin levels in Male and Female Patients with Clinically-Isolated Syndrome or Relapsing-Remitting Multiple Sclerosis." Journal of Neuroendrocrinology 2010; 22: 503-508.

Wehmann, R. and Nisula, B. "Metabolic and Renal Clearance Rates of Purified Human Chorionic Gonadotropin." J. Clin. Invest. copyright The American Society for Clinical Investigation Inc. 0021-9738/81/07/0184/11 vol. 68, pp. 184-194. Jul. 1981.

XP-002582723, NCT00362414 on Aug. 8, 2006: ClinicalTrials.gov Archive.

Barron, A. et al. "Time- and Dose-Dependent Effects of Ovariectomy and Human Chorionic Gonadotropin Treatment on Beta Amyloid and Isoprostane Levels in the PS1M146V Mouse Model of Alzheimer's Disease." P1-436. ICAD Jul./Aug. 2008.

Belayev, L. et al. "Neuroprotective Effect of Human Chorionic Gonadotropin in Transient Focal Cerebral Ischemia in Rats," Poster. International Stroke Conference. San Antonio, TX, Feb. 23-26, 2010.

Belayev, L. et al. "A novel neurotrophic therapeutic strategy for experimental stroke." Brain Research 1280 pp. 117-123 (2009).

Cramer, S. et al. "The Beta-hCG + Erythropoietin in Acute Stroke (BETAS) Study. A 3-Center, Single Dose, Open-Label, Noncontrolled, Phase IIa Safety Trial," Stroke. pp. 1-4. Published online Mar. 4, 2010.

Curtis, M. et al. "Neurogenesis in the Diseased Adult Human Brain," Cell Cycle 2:5, 428-430; Sep./Oct. 2003.

Davidoff, A.W. et al., "Open labeled, uncontrolled pharmacokinetic study of a single intramuscular hCG dose in healthy male volunteers." International Journal of Clinical Pharmacology and Therapeutics, vol. 47: 1-9, Jul. 5, 2009.

Eriksson, P. et al., "Neurogenesis in the adult human hippocampus," Nature Medicine, vol. 4, No. 11: 1313-1317. Nov. 1998.

Garber, Ken. "Stroke treatment—light at the end of the tunnel?" Nature Biotechnology vol. 25, No. 8, Aug. 2007, pp. 838-840.

Kolb, B. et al. "Growth factor-stimulated generation of new cortical tissue and functional recovery after stroke damage to the motor cortex of rats." Journal of Cerebral Blood Flow & Metabolism. pp. 1-15, 2006.

Le Cotonnec, J.Y. et al. "Clinical pharmacology of recombinant human luteinizing hormone: Part II. Bioavailability of recombinant human luteinizing hormone assessed with an immunoassay and an in vitro bioassay," Fertility and Sterility vol. 69, No. 2 Feb. 1998, pp. 195-200.

Mannaerts, B.M.J.L. et al., "A randomized three-way cross-over study in healthy pituitary-suppressed women to compare the bioavailability of human chorionic gonadotrophin (Pregnyl) after intramuscular and subcutaneous administration," Human Reproduction vol. 13 No. 6 pp. 1461-1464, 1998.

Sato, A. et al., "Cystine Knot of the Gonadotropin a Subunit Is Critical for Intracellular Behavior but Not for in Vitro Biological Activity," The Journal of Biological Chemistry. vol. 272, No. 29, Issue of Jul. 18, pp. 18098-18103, 1997.

Woody et al., "Prolactin exerts hematopoietic growth-promoting effects in vivo and partially counteracts myelosuppression by azidothymidine," Experimental Hematology 27: 811-816. 1999.

Greenway et al., "Human choirionic gonadotropin (HCG) in the treatment of obesity," West J. Med. 127(6):461-3 (1977).

Molina-Holgado et al., "Mending the broken brain: neuroimmune interactions in neurogenesis," J. Neurochem. 114(5):1277-90 (2010).

Taoufik et al., "Ischemic neuronal damage," Current Pharm. Design 14(33):3565-73 (2008).

Abstract of DE19905961 A1, "Use of estrogens to treat cardiac insufficiency and left ventricular dysfunction following myocardial infarction," Aug. 17, 2000.

Berlanga, J.J. et al., "Prolactin receptor is associated with c-src kinase in rat liver," Mol. Endocrinol. 1995, vol. 9, No. 11, p. 1461-7.

Database EPODOC European Patent Office, The Hague NL; Jul. 18, 1998, XP002626863, Database accession No. JP1180833 abstract & JP1180833 A (Nippon Kayaku KK) Jul. 18, 1989.

Devito, W.J. et al., "Prolactin-Stimulated Mitogenesis of Cultured Astrocytes," Endocrinology 130(5):2549-2556 (1992).

Di, C.A. et al. "Characterization of prolactin receptor in human brain and choroid plexus," Brain Res., 1992, vol. 570, No. 1-2, p. 341-6.

English translation of Bondarenko, P. "Chorionic Gonadotropin in Treatment of Chronic Circulatory Failure in Patents with Ischemic Heart Disease," Vrach Delo. 1984, vol. 7. pp. 75-78.

Gage, Fred H. and Verman, Inder M. "Stem cells at the dawn of the 21st century," PNAS vol. 100, sup. 1: 11817-11818, Sep. 30, 2003.

Lei, Z.M. et al. "Novel expression of human chorionic gonadotropin/luteinizing hormone receptor gene in brain," Endocrinology, 1993, vol. 132, No. 5, p. 2262-70.

Mountjoy, K. et al. "Prolactin receptors in the rat kidney," J. Endocrinol, 1980, vol. 87, No. 1, p. 47-54.

Ogueta S. et al., "Prolactin is a Component of the Human Synovial Liquid and Modulates the Growth and Chondrogenic Differentiation of Bone Marrow-Derived Mesenchymal Stem Cells", Molecular and Cellular Endocrinology 2002, vol. 190, pp. 51-63.

Ouhtit, A. et al. "Visualization of gene expression of short and long forms of prolactin receptor in the rat," Endocrinology, 1993, vol. 133, No. 1, p. 135-44.

Partial European Search Report in related EP Application No. 11000912.3-1521, Apr. 12, 2011.

Sakaguchi, K. et al. "Differential regulation of prolactin receptor mRNA expression in rat liver and kidney by testosterone and oestradiol," J. Endocrinol, 1994, vol. 143, No. 2, p. 383-92.

Sughara et al., "Biosynthesis of a biologically active single peptide chain containing the human common alpha and chorionic b subunits in tandem," PNAS 92:2041-5 (1995).

Thorne, Rick F. et al. "The role of the CD44 transmembrane and cytoplasmic domains in co-ordinating adhesive and signalling events," Journal of Cell Science 117:373-380, 2004.

Tsai-Morris, C. H. et al. "Structural organization of the rat luteinizing hormone (LH) receptor gene," J Biol Chem, 1991 vol. 266, No. 17, p. 11355-9.

Urbanek et al., "Stem Cell Niches in the Adult Mouse Heart," PNAS Jun. 13, 2006. vol. 103, p. 9226-9231.

Watt, Fiona M. and Hogan, Brigid L.M. "Out of Eden: Stem Cells and Their Niches," Science vol. 287: 1427-1430, Feb. 25, 2000.

XP-002587374 Definition of "Stem Cell" from Wikipedia. Retrieved from "http://web.archive.org/web/20040924012115/http://en.wikipedia.org/wiki/Stem_cell" Printed Jun. 16, 2010.

* cited by examiner

DOSING REGIMENS FOR NEURAL STEM CELL PROLIFERATING AGENTS AND DIFFERENTIATING AGENTS FOR THE TREATMENT OF NEUROLOGICAL DISORDERS

CROSS-REFERENCE TO RELATED APPLICATIONS

This application claims priority to and the benefit of U.S. Provisional Application Ser. No. 60/783,500, filed on Mar. 17, 2006; U.S. Provisional Application Ser. No. 60/789,132, filed on Apr. 5, 2006; and U.S. Provisional Application Ser. No. 60/862,669, filed on Oct. 24, 2006, which are incorporated herein by reference in their entireties.

BACKGROUND

The development of techniques for the isolation and in vitro culture of multipotent neural stem cells (for example, see U.S. Pat. Nos. 5,750,376; 5,980,885; 5,851,832) significantly improved the outlook for the treatment of neurodegenerative diseases and conditions. It was discovered that fetal brains can be used to isolate and culture multipotent neural stem cells in vitro. Moreover, in contrast to the long held belief that adult brain cells are not capable of replicating or regenerating brain cells, it was found that neural stem cells may also be isolated from brains of adult mammals. These stem cells, either from fetal or adult brains, are capable of self-replicating. The progeny cells can proliferate or differentiate into any cell in the neural cell lineage, including neurons, astrocytes and oligodendrocytes. Therefore, these findings not only provide a source of neural cells which can be used in transplantations but also demonstrate the presence of multipotent neural stem cells in adult brain.

Certain agents, neural stem cell proliferating agents, have been found to increase the number of neural stein cells in vitro or in vivo. The mechanisms for such increase may include stimulating proliferation, inhibiting differentiation, and/or preventing death of the neural stem cells. Additional agents, stem cell differentiating agents, have been found to selectively enhance the production of neuronal precursor cells or glial precursor cells in vitro or in vivo. These proliferating and differentiating agents can thus be employed to increase and selectively enhance neurons and glial cells.

SUMMARY

Provided herein are effective dosing regimens for neural stem cell proliferating agents and differentiating agents, kits, and uses thereof. Such compositions of matter and methods can be utilized acutely (e.g., within days after neural injury or onset of neurologic symptoms) or can be used chronically (e.g., for a persisting neural injury or ongoing neurologic symptoms). Furthermore, the compositions and methods can be used continuously or intermittently.

Accordingly, a method for treating or ameliorating a neurodegenerative disease or condition in a mammal is provided. The method comprises administering to the mammal an effective amount of hCG or LH and an effective amount of EPO, wherein the hCG or LH is administered systemically in at least three doses, optionally by use of a kit. The hCG, LH, and/or EPO can be administered either continuously or intermittently. Further, the hCG or LH can be administered in a first treatment period and EPO can be delivered in a second treatment period. For example, hCG or LH can be administered intermittently on days 1, 3, and 5 of a first treatment period, then EPO can be administered continuously on days 1, 2, and 3 of a second treatment period.

Also provided herein is a further method for treating or ameliorating a neurodegenerative disease or condition in a mammal. The method comprises administering to the mammal an effective amount of hCG or LH in a first treatment period followed by an effective amount of EPO in a second treatment period, optionally by use of a kit. The hCG or LH can be delivered intermittently during the first treatment period and the EPO can be delivered continuously during the second treatment period. For example, hCG or LH can be administered intermittently on days 1, 3, and 5 of a first treatment period, then EPO can be administered continuously on days 1, 2, and 3 of a second treatment period.

In the methods and kits, the treatment periods may be, for example, at least three days. The treating methods can be repeated several times or many times with second, third, forth, fifth, etc. treating periods. The treating methods, whether administered once, twice, several, or many times, can take the form of one or more kits.

The details of methods and kits are set forth in the accompanying drawings and the description below. Other features, objects, and advantages of the methods and kits will be apparent from the description and drawings, and from the claims.

BRIEF DESCRIPTION OF FIGURES

Like reference symbols in the various drawings indicate like elements.

DETAILED DESCRIPTION

Figure 1:
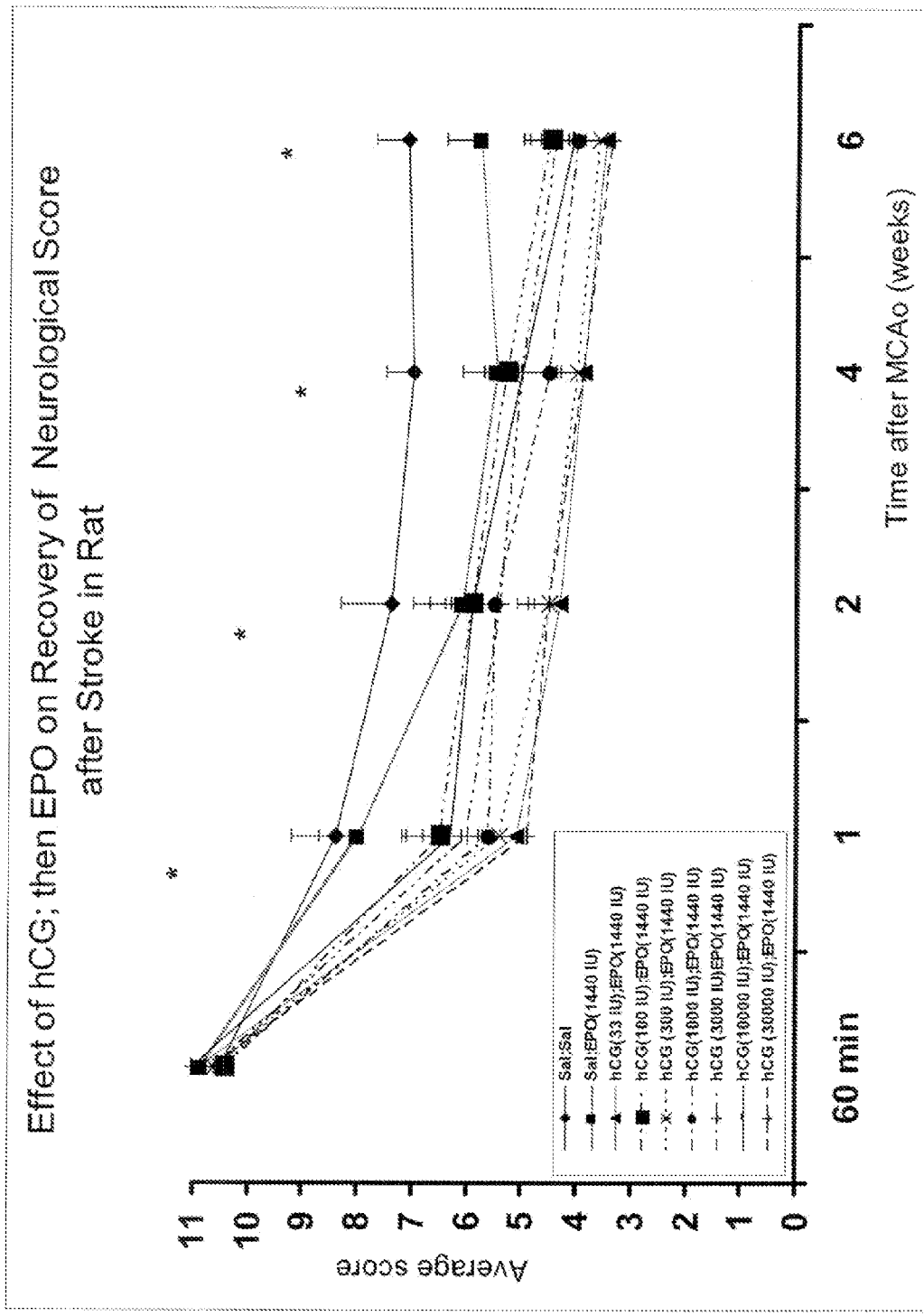
FIG. 1 shows the effect on functional recovery of a rat subjected to a Middle Cerebral Artery occlusion (MCAo) stroke with increasing dosages of hCG with an intravenous (IV) administration of 1440 ID EPO per day following intramuscular (IM) administration of dosages of hCG.

Currently there are no neural stem cell proliferating and differentiating agents that have been clinically approved for use in treatment of neurological diseases or conditions. These agents are useful in treating neurological diseases and conditions, thus there is a need for effective dosing regimens using these agents. Effective dosing regimens for neural stem cell proliferating and differentiating agents, kits comprising effective dosing regimens for neural stem cell proliferating agents, and uses thereof are provided herein. Such kits and methods can be utilized acutely (e.g., within days after injury or onset of a neurodegenerative disease or condition) or can be used, chronically (e.g., for a chronic neurodegenerative disease or condition). Furthermore, the compositions and methods can be used continuously or intermittently as further described below.

The methods described herein use neural stem cell proliferating agents for treating or ameliorating a neurodegenerative disease or condition. In these methods, a neural stem cell proliferating agent is administered over the course of a first treatment period. The neural stem cell proliferating agent can be administered continuously or intermittently during the first treatment period. A neural stem cell differentiating agent can further be added during the first treatment period. The examples and description include the use of neural stem cell proliferating agents (e.g., prolactin, hCG, LH, CSF, G-CSF, GM-CSF, VEGF) and differentiating agents (e.g., EPO, BDNF, BMP, PACAP); however, analogs, fragments, or variants of such agents can similarly be used in any of the methods, devices, or kits taught herein. As a specific example, a method is disclosed in which an effective amount of hCG or LH and an effective amount of EPO are administered to a mammal, wherein the hCG or LH is administered systemically in at least three doses.

These methods for using neural stem cell proliferating agents for treating or ameliorating a neurodegenerative disease or condition can further include administering a neural cell differentiating agent in a second treatment period that starts after the end of the first treatment period. The second treatment period can be at least three days. The neural stem cell differentiating agent can be administered continuously or intermittently during the second treatment period. The second treatment period can begin at least one day after the end of the second treatment period. As a specific example, a method is disclosed in which a neural stem cell proliferating agent is administered continuously at least three times systemically over a first treatment period and a neural stem cell differentiating agent is administered over a second treatment period. As a further example, a method is disclosed in which the first treatment period is five days, the neural stem cell proliferating agent is administered intermittently, a second treatment period starts one day after the end of the first treatment period, and the neural stem cell differentiating agent is administered continuously for at least three days. As an additional example, an effective amount of hCG or LH can be administered in a first treatment period followed by an effective amount of EPO in a second treatment period.

As used herein, to deliver or administer a substance continuously to a subject means to deliver or administer the substance at least once per day for a period of consecutive days. For example, the substance may be administered systemically by injection (e.g., IM or subcutaneously) or taken orally daily at least once per day, or administered by infusion in a manner that results in the daily delivery into the tissue or blood stream of the subject. Optionally, the substance is delivered, by infusion or a means other than infusion. As used herein the term systemically does not include intracerebral ventricular infusion. The duration, or treatment period, during which the substance is continuously delivered or administered can last from three days to several years, even for the rest of a subject's life. For example, the duration may be 3-6 days, 3-14 days, 3-21 days, 3-28 days, 1-4 months, 1-6 months, 1-9 months, 1-12 months, 1-2 years, 1-3 years, 1-5 years, 1-10 years, and the like. For further example the treatment period for continuous delivery can be at least three days, at least four days, at least five days, at least six days, at least seven days, or at least fourteen days. Further, the substance can be delivered consecutively on days 1, 2, and 3 of the administration period.

As used herein, to deliver or administer a substance intermittently to a subject means to deliver or administer the substance less than daily, including, for example, once every 2, 3, 4, 5, or 7 days for a period of time. For example, the substance may be delivered or administered every other day of a treatment period, e.g., on days 1, 3, and 5 of a treatment period. The duration, or treatment, period, during which the substance is intermittently delivered or administered can last from three days to several years, even for the rest of a subject's life. For example, the duration may be 3-6 days, 3-14 days, 3-21 days, 3-28 days, 1-4 months, 1-6 months, 1-9 months, 1-12 months, 1-2 years, 1-3 years, 1-5 years, 1-10 years, and the like. For further example the treatment period for intermittent delivery can be at least three days, at least four days, at least five days, at least six days, at least seven days, or at least, fourteen days.

The methods provided herein, for example, can use the proliferating agents prolactin, hCG, LH, CSF, G-CSF, GM-CSF, or VEGF for treatment of a neurodegenerative disease or condition through administration of an effective amount of the proliferating agent to the subject with a neurodegenerative disease or condition. By way of example, the proliferating agents hCG and LH bind the same receptor, and can be used interchangeably in equipotent doses in the specific examples provided herein. As a further example, the proliferating agent hCG can be administered intramuscularly (IM) at a dose of about 120-200 IU/kg/day followed by intravenous (IV) administration of about 570-950 IU/kg/day of EPO. For further example, an hCG can be intramuscularly administered at a dose of 160 IU/kg/day followed by intravenous administration of 765 IU/kg/day of EPO. Intermittent treatment with hCG and LH optionally comprises several days of hCG or LH administration (e.g., on days 1, 3, 5). Such administration of a neural stem cell stimulating agent can be followed by several days of intermittent (e.g., day 7, 9, 11) or continuous (e.g., on days 7, 8, and 9) administration of a differentiating agent such as EPO. Equipotent doses of other neural stem cell, proliferating agents can also be used in similar regimens.

Thus, Example 4 shows a dosing regimen for prolactin (another proliferating agent). Various amounts of prolactin were administered daily for 6 days and the effects on neural stem cell numbers were examined. The results showed that about 150-200 µg/day (including for example 170 µg/day) was the optimal amount in this dosing schedule. This dosing regimen, about 170 µg/day for 6 days, was then varied by shortening the dosing period (170 µg/day for 3 days) or combining a higher daily dose with a shortened period to achieve a similar total dose (about 396 µg/day for 3 days). The results indicated that the continuous delivery of a lower dose over a longer period time is effective.

The methods including continuous delivery or intermittent delivery provided herein can improve neurologic status. Without meaning to be limited, this improvement can be related to an increase in the number of neural stem cells in a mammal. The efficacy of an effective amount of a neural stem cell proliferating agent can be optimized to increasing the number of neural stem cells or the neurologic status in a mammal. The methods comprise administering the neural stem cell proliferating agent to the mammal continuously or intermittently for a period of time, wherein the total dosage of the neural stem cell proliferating agent administered in said period, of time equals the effective amount, and wherein, the agent is administered at least three times over the first treatment period.

The methods described herein can be optimized to increase the efficacy of an effective amount of a neural stem cell proliferating agent in treating or ameliorating a neurodegenerative disease or condition in a mammal. The methods comprise administering the neural stem cell proliferating agent to the mammal continuously or intermittently for a period of time, wherein the total dosage of the neural stem cell proliferating agent administered in said period of time equals the effective amount, and wherein the agent is administered at least three times over the first treatment period.

The neural stem cell proliferating agent can be administered to the mammal within about 14 days (e.g., 0 to about 14 days) of a central nervous system (CNS) injury, onset of symptoms, or diagnosis. As used herein 0 days refers to the time of CNS injury, onset of symptoms, or diagnosis. Optionally, the neural stem cell proliferating agent can be administered within about 13, 12, 11, 10, 9, 8, 7, 6, 5, 4, 3, 2, or 1 day(s) (e.g., 0 to about 5 days) of a CNS injury, onset of symptoms, or diagnosis. Optionally, the neural stem cell proliferating agent can be administered to the mammal within 24 hours of a CNS injury, onset of symptoms, or diagnosis. Optionally, the neural stem cell proliferating agent can be administered to the mammal within 12, 11, 10, 9, 8, 7, 6, 5, 4, 3, 2, 1 hour(s) of a CNS injury, onset of symptoms, or diagnosis.

For intermittent treatment, higher doses of the agent can be used, or continuous treatment can be used. In particular, neural stem cell proliferating agents can be delivered to mammalian subjects at a low dose in a continuous fashion, as opposed to the administration of a high-dose intermittently. The neural stem cell proliferating agent(s) optionally is/are delivered within 24 to 72 hours after neural injury or the onset of neurological symptoms. Optionally, continuous administration of neural stem cell proliferating agents is for 2-5 days. For example, for a given total effective dose of prolactin, or analogs, fragments or variants of prolactin, a dosing regimen comprising daily delivery of ⅙ of the total amount for six days was more effective than delivering ⅓ of the total amount daily for three days. Equipotent doses of other neural stem cell proliferating agents can be used in similar paradigms.

The methods described herein can also include monitoring levels of the neural stem cell proliferating agent or neural stem cell differentiating agent in a biological fluid of the mammal. The biological fluid monitored can be, for example, cerebral spinal fluid or blood. For example, the level of hCG (or another neural stem cell proliferating agent or neural stem cell differentiating agent) in blood serum can be measured after administration either during or after a treatment period. Equipotent levels of various neural stem cell proliferating agent or neural stem cell differentiating agent can be both determined and monitored in biological fluid.

Also provided herein is a kit far the treatment or amelioration of a neurodegenerative disease or condition in a mammal. The kit comprises at least three dosage units of a neural stem cell proliferating agent for administration during a first treatment period. The total dosage of the neural stem cell proliferating agent administered in that first treatment period can equal an effective amount. The treatment period can be at least three days. The kit can include instructions for use of the kit. The instructions can be for continuous administration or for intermittent administration of the neural stem cell proliferating agent.

The kit can further provide at least three dosage units of a differentiating agent. The differentiating agent can be used over the first treatment period. The total dosage of the differentiating agent administered in the first treatment period can equal an effective amount. The treatment period can be at least three days. The treatment period for the differentiating agent optionally is a second or subsequent treatment period that follows the treatment period or periods with the neural stem cell proliferating agent. The kit can include instructions for use of the differentiating agent. The instructions can be for continuous administration or for intermittent administration of the neural stem cell proliferating agent.

The total dosage of each of the neural stem cell proliferating agent differentiating agent, or other agents in the kit can be provided in one container, a plurality of containers, or any combination thereof. For example, the total dosage for the neural stem cell proliferating agent or agents can be in one container suitable for providing a metered dose or suitable for extraction of a dose, for example, by the person to be treated or by another person, such as a caregiver. Instead of a single container, the neural stem cell proliferating agent or agents can be present in a plurality of containers that provide aliquots for doses suitable for administration daily, weekly, monthly, or the like. A single container or a plurality of containers for the differentiating agent or other agents can similarly be provided in the kit. Combinations may also be included whereby one container of neural stem cell proliferating agent(s) but a plurality of differentiating agent(s) containers or the opposite may be included in the kit. Also, the total dosage of a neural stem proliferating factor for a first treating period may be in a single container or a plurality of containers, the total dosage for a second treating period may be in a single container or a plurality of containers, or any combination thereof.

The neural stem cell proliferating agent and the differentiating agent can optionally be packaged in a kit, such that the total amount, of the neural stem cell proliferating agent and the differentiating agent to be delivered during the treating period(s) is contained in the kit. The kit can optionally contain other components or combinations of other components, including for example a blood sampling device or a component thereof.

The kit can further comprise a device or means for monitoring hematocrit levels in a patient or a suitable device for removing an amount of blood from the patient or both a monitor and a blood sampling device. Blood sampling and monitoring is desirable because hematocrit levels may rise above acceptable levels. Acceptable hematocrit levels can be determined by any standard established in the art.

Optionally, a drug delivery device for administration can be included in a kit containing the neural stem cell proliferating agent(s) and/or the differentiating agent(s).

The kit can be suitable for use in a health care facility such as an inpatient care facility or an emergency care facility. A health care facility includes, for example, a hospital. The kit is also suitable for use after discharge from or without admission in an the inpatient care facility. Packaging in the form of a kit advantageously facilitates early release of patients from a health care facility by permitting patient treatment at a long term care facility or at home, for example, by self-treatment, outpatient treatment, or treatments by a caregiver or health care provider in a home, a long term care facility, or the like. Similarly, packaging in the form of a kit allows immediate treatment of a patient in an acute situation, including an emergency room or by an on-site emergency care provider (e.g., by an emergency medical technician, an athletic trainer, or the like).

In the methods and kits, the period of time may be, for example, at least three, four, five, six, seven, eight, nine, ten, eleven, twelve, fourteen, twenty one, twenty eight days, or any number of days between 3 and 28. Optionally, the methods and kits may comprise administering to the mammal the neural stem cell proliferating agent continuously in a second treating period, wherein the second treating period starts after the end of the period of time by an interval of at least one, two or three days, and wherein the second treating period is at least three days. The second treating period, like the first treating period, may be, for example, at least three, four, five, six, seven, eight, nine, ten, eleven, twelve, fourteen, twenty one, or twenty eight days. The interval between the first treating period and the next treating period may also be, for example, at least one, two, three, four, five, six, seven, eight, nine, ten, eleven, twelve, fourteen, twenty one, or twenty eight days. This treating schedule can be repeated several times or many times. The neural stem cell proliferating agent used in the second or subsequent treating period may be the same as or different than the neural stem cell proliferating agent used in the first treating period or used in other treating periods. Furthermore, more than one neural stem cell proliferating agent may be used in a single treating period. Thus, kits useful in the methods may contain one or more neural stem cell proliferating agents for one or more treating periods.

The neural stem cell proliferating agent(s) or other agents (e.g., differentiating agents) can be administered by any method established in the art, such as by intravenous, infra-arterial, intracolonical, intratracheal, intraperitoneal, intranasal, intravascular, intrathecal, intracranial, intramarrow, intrapleural, intradermal, subcutaneous, intramuscular, oral, topical administration, pulmonary administration, or any combination thereof. Optionally, the drug delivery device or component thereof for administration can be included in a kit containing the neural stem cell proliferating agent.

The neural stem cell proliferating agent may be any substance that is capable of increasing the number of mammalian neural stem cells, in vitro or in vivo. As used herein a promoting agent has the same meaning as a proliferating agent. Agents that can increase neural stem cell number include, but are not limited to:

1. Follicle-stimulating hormone (FSH), which often acts in concert with LH and induces LH receptor expression, thereby enhancing the effects of LH signaling.
2. Growth hormone (GH), which can stimulate neural stem cell proliferation.
3. Insulin growth factors (IGFs), including IGF-1, which are somatomedians that are released from many tissues in response to GH and mediate many of the growth proliferating effects of GH and which stimulate neural stem cell proliferation.
4. Growth hormone releasing hormone (GHRH), which is secreted from the hypothalamus and induces GH release from the anterior pituitary, resulting in increased levels of circulating GH.
5. Prolactin (PRL), which is secreted from the anterior pituitary and which is promotes neural stem cell proliferation.
6. Prolactin releasing peptide (PRP), which triggers the release of prolactin.
7. Fibroblast growth factor (FGF), a mitogenic agent for neural stem cells.
8. Estrogen, which promotes the proliferation of neural stem cells, including for example in the hippocampus.
9. Serotonin, which promotes the proliferation of neural stem cells in the hippocampus.
10. Epidermal growth factor (EGF), a mitogenic agent for neural stem cells.
11. Transforming growth factor alpha (TGFα), a mitogenic agent for neural stem cells.
12. Gonadotropin releasing hormone (GnRH), which triggers the release of LH.
13. Ciliary neurotrophic factor (CNTF) and leukemia inhibitory factor (LIF) which signal via the gp130 subunit by a signaling pathway that promotes neural stem cell self-renewal, thereby expanding the neural stem cell population of the brain.
14. Colony stimulating factor (CSF).
15. Granulocyte colony stimulating factor (G-CSF).
16. Granulocyte-macrophage colony stimulating factor (GM-CSF).
17. Vascular, endothelial growth factor (VEGF).
18. Lutenizing hormone (LH).
19. Human chorionic gonadotropin (hCG).

Furthermore, neural cell differentiating agents can be administered to selectively enhance neuron formation or glial cell formation. These differentiating agents can also be delivered according to the dosing regimens and kits. Exemplary differentiating agents include, but are not limited to:

1. Erythropoeitin (EPO), which enhances neural stem cell commitment to neuronal cell lineage and is useful for treating mouse and rat models of stroke.
2. Brain derived neurotrophic factor (BDNF), which is a known survival factor and differentiating agent that promotes the neuronal lineage.
3. Transforming growth factor beta and bone morphogenetic proteins (BMPs), which are differentiating agents that promote the neuronal lineage and the generation of specific neuronal phenotypes (e.g., sensory interneurons in the spinal cord).
4. Thyroid hormone (TH, including both the T3 and T4 forms), a differentiating agent that promotes the maturation and generation of oligodendrocytes. See, e.g., Rodriguez-Pena, 1999.
5. Thyroid stimulating hormone (TSH) and Thyroid releasing hormone (TRH), which promote the release of TH from the anterior pituitary resulting in increased levels of circulating TH. This agent could be used in combination with LH or hCG to promote oligodendrogliogenesis from neural stem cells.
6. Sonic hedgehog (SHH), a morphogen that patterns the developing CNS during development and, in different concentrations, promotes the generation of specific types of neurons (e.g., motor neurons in the spinal cord) and oligodendrocytes. This agent could be used in combination with LH or hCG to promote neurogenesis and/or oligodendrogliogenesis from, neural stem cells.
7. Platelet derived growth factor (PDGF), which promotes the generation and differentiation of oligodendrocytes from neural stem cells. This agent could be used in combination with LH or hCG to promote oligodendrogliogenesis from neural stem cells.
8. Cyclic AMP and agents which enhance the cAMP pathway, such, as pituitary adenylate cyclase activating polypeptide (PACAP) and serotonin, which selectively promote neuron production.

Any of the methods and kits can comprise a plurality of neural stem cell proliferating agents and/or neural cell differentiating agents. Thus, one or more neural stem cell proliferating agents can be administered together or sequentially and can be administered via separate compositions or in combination within a single composition. Further, one or more neural stem cell proliferating agents and one or more neural stem cell differentiating agents can be administered together or sequentially and can be administered via separate compositions or in combination within a single composition. For example, PRL and LH or hCG can be used in combination to maximize neural stem cell proliferation; PRP can be used in combination with LH or hCG to maximize neural stem cell proliferation; GnRH can be used in combination with or in place of LH or hCG to increase circulating levels of LH and enhance neural stem cell proliferation; and CNTF and LIP can be used in combination with LH or hCG to promote neural stem cell proliferation and increase the size of the neural stem cell population within the CNS. Further for example, prolactin can be used with EPO, LH can be used with EPO, and hCG can be used with EPO. All other combinations, not explicitly set forth, can also be used.

Appropriate dosages for the factors can be determined according to established methods in the art. For example, the dosage for prolactin may range from about 0.510 IU/kg/day to about 100,000 IU/kg/day, such as, for example, about 0.510-100,000; 0.510-75,000; 0.510-50,000; 0.510-25,000; 0.510-10,000; 100-5,000; 100-2,000; 500-2,000; 1,000-2,000; 100-1,000; 200-800 IU/kg/day. The dosage for hCG can range from about 0.5 IU/kg/day to about 3,000,000 IU/kg/day, such as, for example, about 0.5-2,000,000; 0.5-1,000,000; 0.5-500,000; 0.5-250,000; 0.5-100,000; 0.5-50,000; 10-25,000; 10-10,000; 240-216,000; 1,200-2,000; 2,160; or 1,600 IU/kg/day. hCG can also be provided at a dose of 10,000 IU/day. The dosage for LH can range from about 0.5 IU/kg/day to about 500,000 IU/kg/day, such as, for example, about 0.5-300,000; 0.5-200,000; 0.5-100,000; 0.5-50,000; 0.5-25,000; 24-21,600; 1,000; 120-200; 216; or 160 IU/kg/day. LH can also be provided at a dose of 10,000 IU/day. The dosage for EPO can range from about 100 IU/kg/day to about 2000 IU/kg/day, such as, for example, about 100-1500; 100-1000; 160-1000; 570-950; 765; or 1020 IU/kg/day. EPO can also be provided at a dose of 30,000 IU/day. Equipotent doses of other agents can be used. The dosage here refers to the average dose delivered every day or intermittently during the entire treating period. For example, if the neural stem cell proliferating agent or differentiating agent is not delivered everyday, the total amount of the delivered agent during the entire treating period can be divided by the total number of days in the treating period, including intervals, to arrive at the daily dosage.

Specific dosage units (i.e., the amount or a single administration within a series of administrations in a treatment period) can be specified for a neural stem cell proliferating or differentiating agents to be used with the methods disclosed herein. These dosage units can be within the specific dosages and dosage ranges specified herein. Dosage units can be defined with respect to the amount that must be administered to achieve a desired level of a neural stem cell proliferating or differentiating agent in a subject. For example, a dosage unit of a neural stem cell proliferating agent that provides a neural stem cell proliferating or differentiating agent level in blood serum of 0.03 IU/L to 5,000,000 IU/L. Or, as a further example, a dosage unit of a neural stem cell proliferating or differentiating agent that provides a proliferating agent level in cerebral spinal fluid of about 0.003 IU/L to about 5,000 IU/L.

When the neural stem cell proliferating agent and the differentiating agent are administered systemically, a blood brain barrier permeabilizer can be optionally included in the kits or used in the methods to facilitate entry into the brain. Blood brain barrier permeabilizers are known in the art and include, by way of example, bradykinin and the bradykinin agonists described in U.S. Pat. Nos. 5,686,416; 5,506,206 and 5,268,164 (such as $NH_2$-arginine-proline-hydroxyproxproline-glycine-thienylalanine-serine-proline-4-Me-tyrosine.ψ (—$CH_2NH$)-arginine-COOH).

Alternatively, the neural stem cell proliferating agent or the differentiating agent to be delivered can be conjugated to a transferrin receptor antibody as described in U.S. Pat. Nos. 6,329,508; 6,015,555; 5,833,988 or 5,527,527. The neural stem cell proliferating agent and fee differentiating agent can also be delivered as a fusion protein comprising the neural stem cell proliferating or differentiating, agent and a ligand that is reactive wife a brain capillary endothelial cell receptor, such as the transferrin receptor (see, e.g., U.S. Pat. No. 5,977,307).

The pharmaceutical compositions can be prepared by mixing the desired therapeutic agents with an appropriate vehicle suitable for the intended route of administration, optionally for use in an appropriate drag delivery device. In making the pharmaceutical compositions of this invention, the therapeutic agents are usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the therapeutic agent. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the therapeutic agents, soft and hard gelatin capsules, suppositories, sterile injectable solutions, and sterile packaged powders.

Some examples of suitable excipients include artificial cerebral spinal fluid, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include; lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the therapeutic agents after administration, to the patient by employing procedures known in the art.

For preparing solid compositions such as tablets, the therapeutic agent is mixed with a pharmaceutical excipient to form a solid preformulation composition containing a homogeneous mixture of a compound of the present invention. When referring to these preformulation compositions as homogeneous, it is meant that the therapeutic agents are dispersed evenly throughout the composition so that the composition may be readily subdivided into equally effective unit dosage forms such as tablets, pills and capsules. The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist, disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. The compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine.

Solution, suspension, or powder compositions may be administered, preferably orally or nasally, from drug delivery devices which deliver the formulation in an appropriate manner. Another formulation employed in the methods of the present invention employs transdermal delivery devices ("patches"). Such transdermal patches may be used to provide continuous or discontinuous infusion of the therapeutic agent of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents. Other suitable formulations for use in the present invention can be found in Remington's Science and Practice of Pharmacy, 21st Edition, ed. University of the Sciences in Philadelphia, Lippincott Williams & Wilkins, Philadelphia Pa., 2005.

A mammal treated using the methods and kits described herein can be of any age, including a child, juvenile or an adult.

The terms used in this application are defined as follows unless otherwise indicated.

A neural stem cell or neural stem cell is a stem cell in the neural cell lineage. A stem cell is a cell which is capable of reproducing itself. In other words, daughter cells which result from stem cell divisions include stem cells. The neural stem cells are capable of ultimately differentiating into all the cell types in the neural cell lineage, including neurons, astrocytes and oligodendrocytes, astrocytes and oligodendrocytes are collectively called glia or glial cells. Thus, the neural stem cells referred to herein are multipotent neural stem cells.

A neural stem cell proliferating agent is a substance that is capable of increasing the number of neural stem cells, for example, by stimulating proliferation, inhibiting differentiation, and/or preventing death of neural stem cells.

A neurodegenerative disease or condition is a disease or medical condition associated with neuron loss or dysfunction. Examples of neurodegenerative diseases or conditions include neurodegenerative diseases, central nervous system injuries or dysfunctions. Neurodegenerative diseases include, for example, Alzheimer's disease or other dimentia, multiple sclerosis (MS), schizophrenia, macular degeneration, glaucoma, diabetic retinopathy, peripheral neuropathy, Huntington's disease, amyotrophic lateral sclerosis, and Parkinson's disease, CNS injuries include, for example, cerebrovascular events like strokes (e.g., hemorrhagic strokes, focal ischemic strokes or global ischemic strokes), ocular ischemia, and dural sinus thrombosis; traumatic brain or spinal cord injuries (e.g., injuries caused by a brain or spinal cord surgery or physical accidents); concussion; injury caused by drugs, (e.g., chemotherapeutics, recreational drugs, and neuroleptics); coronary artery bypass graft (CABG) surgery; and ischemia at child birth. CNS dysfunctions include, for example, depression, epilepsy, neurosis and psychosis. Examples of neurodegenerative conditions include aging. The number of neural stem cells in the subventricular zone is significantly reduced in aged mice. Accordingly, amelioration of problems associated with aging is achieved by administering neural stem cell proliferating agents and, optionally, neural stem cell differentiating agents according to the methods and kits.

Treating and ameliorating mean the reduction or complete removal of one or more symptoms (including neurologic symptoms or behavioral performance) of a disease or medical condition. Such treatment or amelioration can include the delay or elimination of the onset of one or more symptoms when, administered to a person at risk for the disease or medical condition. Tests for the success of treatment or amelioration are well known in the art.

A polypeptide which shares substantial sequence similarity with a native factor is at least about 30% identical with the native factor at the amino acid level. The polypeptide is preferably at least about 40%, more preferably at least about 60%, yet more preferably at least about 70%, and most preferably at least about 80% identical with the native factor at the amino acid level. Thus, substantial similarity can constitute about 30-99% identity.

The phrase percent identity or % identity of an analog or variant with a native factor refers to the percentage of amino acid sequence in the native factor which are also found in the analog or variant when the two sequences are aligned. Percent identity can be determined by any methods or algorithms established in the art, such as LALIGN or BLAST.

A polypeptide possesses a biological activity of a native factor if it is capable of binding to the receptor for the native factor or being recognized by a polyclonal antibody raised against the native factor. Preferably, the polypeptide is capable of specifically binding to the receptor for the native factor in a receptor binding assay.

A functional agonist of a native factor is a compound that binds to and activates the receptor of the native factor, although it does not necessarily share a substantial, sequence similarity with the native factor.

A lutenizing hormone or LH is a protein comprising a native mammalian (e.g., human) LH or a peptide sequence comparable to a native mammalian LH. As used herein, an LH analog, variant, or fragment (1) comprises a polypeptide that shares substantial sequence similarity with a native mammalian LH, preferably the native human LH; and (2) possesses a biological activity of the native mammalian LH. The native mammalian LH is a gonadotropin secreted by the anterior lobe of the pituitary. LH is a heterodimer consisting of non-covalently bound alpha and beta subunits. The alpha subunit is common among LH, FSH and hCG, and the beta subunit is specific for each hormone. The LH useful in the present methods and kits may have the native alpha subunit, with the beta subunit sharing a substantial sequence similarity with a native mammalian LH. Alternatively, the LH may have the native beta subunit, with the alpha subunit sharing a substantial sequence similarity with a native mammalian LH. The LH analog, variant, or fragment may also have both the alpha and beta subunit sharing a substantial sequence similarity with a native, corresponding subunit. Thus, the term LH analog or variant comprises a deletional, insertional, or substitutional mutant of a native LH subunit. Furthermore, the term LH encompasses the LHs from other species and the naturally occurring variants thereof. In addition, an LH analog may also be a functional agonist of a native mammalian LB receptor.

A human chorionic gonadotropin or hCG is a protein comprising a native mammalian hCG (e.g., human) or a polypeptide sequence comparable to a native mammalian hCG. As used herein, an hCG analog, variant, or fragment (1) comprises a polypeptide that shares substantial sequence similarity with the native hCG; and (2) possesses a biological activity of the native hCG. The native hCG is a heterodimer consisting of non-covalently bound alpha and beta subunits. The alpha subunit is common among LH, FSH and hCG, and the beta subunit is specific for each hormone. However, the beta subunits of hCG and LH share an 85% sequence similarity. The hCG useful in the present methods and kits may have the native alpha subunit, with the beta subunit sharing a substantial sequence similarity with the native hCG. Alternatively, the hCG may have the native beta subunit, with the alpha subunit sharing a substantial sequence similarity with the native hCG. The hCG analog, variant, or fragment may also have both the alpha and beta subunit sharing a substantial sequence similarity with the native, corresponding subunit. Thus, the term hCG analog, variant, or fragment comprises a deletional, insertional, or substitutional mutants of a native hCG subunit. Furthermore, the term hCG encompasses the hCG counterparts from other species and the naturally occurring variants thereof. In addition, an hCG analog may also be a functional agonist of a native mammalian hCG/LH receptor.

A prolactin is a polypeptide comprising a native mammalian prolactin (e.g., human) or a polypeptide sequence comparable to a native mammalian prolactin. As used herein, a prolactin analog, variant, or fragment (1) shares substantial sequence similarity with a native mammalian prolactin, preferably the native human prolactin; and (2) possesses a biological, activity of the native mammalian prolactin. The native human prolactin is a 199 amino acid polypeptide synthesized mainly in the pituitary gland. Thus, the term prolactin encompasses prolactin analogs, variants, or fragments that are the deletional, insertional, or substitutional mutants of the native prolactin. Furthermore, the term prolactin encompasses the prolactins from other species and the naturally occurring variants thereof.

In addition, a prolactin analog, variant, or fragment may also be a functional agonist of a native mammalian prolactin receptor. For example, the functional agonist may be an activating amino acid sequence disclosed in U.S. Pat. No. 6,333,031 for the prolactin receptor; a metal complexed receptor ligand with agonist activities for the prolactin receptor (U.S. Pat. No. 6,413,952); G120RhGH, which is an analog of human growth hormone but acts as a prolactin agonist (Mode et al., 1996); or a ligand for the prolactin receptor as described in U.S. Pat. Nos. 5,506,107 and 5,837,460.

An epidermal growth factor or EGF is a protein comprising a native mammalian EGF or a polypeptide sequence comparable to a native mammalian EGF. As used herein, an EFG analog, variant, or fragment shares a substantial amino acid sequence similarity with a native EGF, as well as at least one biological activity with the native EGF, such as binding to the EGF receptor. Particularly included as an EGF is the native EGF of any species, TGFα, or recombinant modified EGF. Specific examples include, but are not limited, to, the recombinant modified. EGF having a deletion of the two C-terminal amino acids and a neutral amino acid substitution at position 51 (particularly EGF51 gln51; U.S. Patent Application Publication No. 20020098178A1), the EGF mutein (EGF-$X_{16}$) in which the His residue at position 16 is replaced with a neutral or acidic amino acid (U.S. Pat. No. 6,191,106), the 52-amino acid deletion mutant of EGF which lacks the amino terminal residue of the native EGF (EGF-D), the EGF deletion mutant in which the N-terminal residue as well as the two C-terminal residues (Arg-Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs, variants, and fragments are described in U.S. Patent Application Publication No. 20020098178A1, and U.S. Pat. Nos. 6,191,106 and 5,547,935.

In addition, an EGF analog, variant, or fragment may also be a functional agonist of a native mammalian EGF receptor. For example, the functional agonist may be an activating amino acid sequence disclosed in U.S. Pat. No. 6,333,031 for the EGF receptor, or an antibody that has agonist activities for the EGF receptor (Fernandez-Pol, 1985 and U.S. Pat. No. 5,723,115).

A pituitary adenylate cyclase activating polypeptide or PACAP is a polypeptide comprising a native mammalian PACAP (e.g., human) or a polypeptide sequence comparable to a native mammalian PACAP. As used herein, a PACAP analog, variant, or fragment is a native PACAP or any PACAP analog, variant, or fragment that shares a substantial amino acid sequence similarity with a native PACAP, as well as at least one biological activity with the native PACAP, such as binding to the PACAP receptor. Useful PACAP analogs, variants, and fragments include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563.

In addition, a PACAP analog, variant, and fragment may also be a functional agonist of a native mammalian PACAP receptor. For example, the functional agonist may be maxadilan, a polypeptide that acts as a specific agonist of the PACAP type-1 receptor (Moro et al., 1997).

An erythropoietin or EPO is a protein comprising a native mammalian EPO (e.g., human) or a polypeptide sequence comparable to a native mammalian EPO. As used herein, an EPO analog, fragment, or variant shares a substantial amino acid sequence similarity with a native EPO, as well as at least one biological activity with the native EPO, such as binding to the EPO receptor. Examples of EPO analogs, variants, and fragments are disclosed, for example, in U.S. Pat. Nos. 6,048,971 and 5,614,184.

In addition, an EPO analog, variant, or fragment may also be a functional agonist of a native mammalian EPO receptor. For example, the functional agonist may be EPO mimetic peptide 1 (EMP1; Johnson et al., 2000); one of the short peptide mimetics of EPO as described in Wrighton et al., 1996 and U.S. Pat. No. 5,773,569; any small molecular EPO mimetic as disclosed in Kaushansky, 2001; an antibody that activates the EPO receptor as described in U.S. Pat. No. 5,885,574, WO 96/40231, WO 97/48729, Fernandez-Pol. 1985 or U.S. Pat. No. 5,723,115; an activating amino acid sequence as disclosed in U.S. Pat. No. 6,333,031 for the EPO receptor; a metal complexed receptor ligand with agonist activities for the EPO receptor (U.S. Pat. No. 6,413,952), or a ligand for the EPO receptor as described in U.S. Pat. Nos. 5,506,107 and 5,837,460.

A LH/hCG-inducing agent is a substance that, when given to an animal, is capable of increasing the amount of LH or hCG in the animal. For example, LH-releasing hormone (LHRH) stimulates the secretion of LH.

A mammalian pheromone can be a protein or a small molecule comprising a native mammalian pheromone (e.g., human) or a polypeptide sequence or analogous small molecule comparable to a native mammalian pheromone. As used herein, a pheromone analog, variant, or fragment is a substance that serves as a signal to another animal of the same species, usually the opposite gender. Preferably, the pheromone is selected from the group consisting of 2-sec-butyl-4,5-dihydrothiazole (SET), 2,3-dehydro-exo-brevicomin (DHB), alpha and beta farnesenes, 6-hydroxy-6-methyl-3-heptanone, 2-heptanone, trans-5-hepten-2-one, trans-4-hepten-2-one, n-pentyl acetate, cis-2-penten-1-yl-acetate, 2,5-dimethylpyrazine, dodecyl propionate, and (Z)-7-dodecen-1-yl acetate (see, e.g., Dulac et al., 2003).

An effective amount is an amount of a therapeutic agent sufficient to achieve the intended purpose. For example, an effective amount of an LH or hCG to increase the number of neural stem cells is an amount sufficient, in vivo or in vitro, as the ease may be, to result in an increase in neural stem cell number. An effective amount of an LH or hCG to treat or ameliorate a neurodegenerative disease or condition is an amount of the LH/hCG sufficient to reduce or remove one or more-symptoms of the neurodegenerative disease or condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

An equipotent amount of a neural stem cell proliferating agent is the amount of a neural stem cell proliferating agent required to obtain the same or equivalent effect as another neural stem cell proliferating agent. Equipotent amounts can be specified by a relative level or result of an equipotent amount. Thus, an equipotent amount or dose could be the amount or dose of a neural stem cell proliferating agent required to obtain the same level in blood serum or cerebral spinal fluid as another, specific neural stem cell proliferating agent.

A drug delivery device is an object suitable for administration of an effective amount of a neural stem cell proliferating agent or a differentiating agent. A drug delivery device can effect administration of neural stem cell proliferating agent or a differentiating agent by any method established in the art, including, for example, parenteral, intravenous, infra-arterial, intracolonical, intratracheal, intraperitoneal, intranasal, intravascular, intrathecal, intracranial, intramarrow, intrapleural, intradermal, transdermal, subcutaneous, intramuscular, intraperitoneal, oral, rectal, vaginal, topical administration, pulmonary administration, or any combination thereof. Systemic delivery can be accomplished by techniques including, for example, parenteral, intravenous, intra-arterial, intracolonical, intratracheal, intraperitoneal, intranasal, intravascular, intrathecal, intracranial, intramarrow, intrapleural, intradermal, transdermal, subcutaneous, intramuscular, intraperitoneal, oral, rectal, vaginal, topical administration, pulmonary administration, or any combination thereof. A drug delivery device can be for example, an implantable device or a pump (e.g., an osmotic pump), depot (slow release) delivery of formulation, or an injector pen (with or without a needle). Optionally, the drug delivery device is an infusion device or component thereof or, alternatively, is a device for other means than infusion.

The examples below are intended to further illustrate certain embodiments of the invention, and are not intended to limit the scope of the claims.

EXAMPLES

In the examples below, the following abbreviations have the following meanings. Abbreviations not defined have their generally accepted meanings.
° C.=degree Celsius
hr=hour
min=minute
μM=micromolar
mM=millimolar
M=molar ml milliliter
μl=microliter
mg=milligram
μg=microgram
FBS=fetal bovine serum
PBS=phosphate buffered saline
DMEM=Dulbecco's modified Eagle's medium
MEM=modified Eagle's medium EGF=epidermal growth factor
NSC=neural stem cell
SVZ=sub ventricular zone
PACAP=pituitary adenylate cyclase activating polypeptide
BMP=bone morphogenetic protein
RSA=rat serum albumin Example 1

Functional Improvement Post-Stroke Using rhCG+EPO

Male rats were injured through temporary occlusion of the right middle cerebral artery (MCA), following which increasing doses of recombinant Human chorionic gonadotropin (rhCG) were administered, followed by 3 days of Erythropoietin (EPO, Epogen 1440 IU/day).

Male Long Evans rats (280-330 g) were fasted overnight but allowed free access to water. Atropine sulfate (0.5 mg/kg, i.p.) was injected 10 min before anesthesia. Anesthesia was induced with 3.5% isoflurane in a mixture of 70% nitrous oxide and 30% oxygen. All rats were orally intubated and mechanically ventilated. During ventilation, the animals were paralyzed with pancuronium bromide (0.6 mg/kg, i.p.).

The MCA was temporarily occluded for 90 minutes as described by Zea Longa et al. (*Stroke* 20:84 (1989)) and modified (Belayev et al., *Stroke* 27:1616 (1996)). Following suture placement, the neck incision was closed, and animals were allowed to awaken from anesthesia. At 60 min following MCAo, they were tested on a standardized neurobehavioral battery to confirm the presence of a neurological deficit (Belayev et al, 1996). Rats that did not demonstrate a left upper extremity paresis (total neurological score less than 9; See behavioral tests, below and FIG. 1) were excluded from further study. After 90 min of MCAo, rats were re-anesthetized, temperature probes were re-inserted, and the intraluminal suture were carefully removed.

Behavioral tests were performed in all rats before MCAo and during occlusion (at 60 min) to confirm success of the MCAo. The battery consisted of 2 tests used previously to evaluate various aspects of neurologic function: (1) the postural reflex test, developed by Bederson et al. (*Stroke* 17:472 (1986)) to examine upper body posture while the animal is suspended by the tail; and (2) the forelimb placing test,—developed by De Ryck et al. (*Stroke* 20:1383 (1989)) to examine sensorimotor integration in forelimb placing responses to visual, tactile and proprioceptive stimuli. Neurological function was graded on a scale of 0-12 (normal score=0, maximal score=12).

Treatment and experimental groups are as follows:
Group 1: n=8; Saline solution (of equal volume to hCG administered IM) administered IM on days 1, 3, and 5, followed by administration of saline IV by ALZET® Pump (Alzet Osmotic Pumps; Cupertino, Calif.) beginning day 7,8,9 after surgery. The first injection was administered 24 hours after stroke surgery.
Group 2: n=8; Saline solution (of equal volume to hCG administered IM) administered IM on days 1, 3, and 5, after MCA occlusion followed by administration, of EPO (1440 IU/day) IV by ALZET® Pump beginning day 7, 8, 9. The first injection was administered 24 hours after stroke surgery.
Group 3: n=8; hCG (33 IU/day) delivered by IM on days 1,3, and 5 after MCA occlusion followed by administration of EPO (1440 IU/day) IV by ALZET® Pump beginning day 7, 8, 9. The first injection was administered 24 hours after stroke surgery.
Group 4: n=8; hCG (100 IU/day) delivered by IM on days 1, 3, and 5 after MCA occlusion followed by administration of EPO (1440 IU/day) IV by ALZET® Pump beginning-day 7, 8, 9. The first injection was administered 24 hours after stroke surgery.
Group 5: n=8; hCG (300 IU/day) delivered by IM on days 1, 3, and 5 after MCA occlusion followed by administration, of EPO (1440 IU/day) IV by ALZET® Pump beginning day 7, 8, 9. The first injection was administered 24 hours after stroke surgery.
Group 6: n=8; hCG (1000 IU/day) delivered by IM on days 1, 3, and 5 after MCA occlusion followed by administration of EPO (1440 IU/day) TV by ALZET® Pump beginning day 7, 8, 9. The first injection was administered 24 hours after stroke surgery.
Group 7: n=8; hCG (3000 IU/day) delivered by IM on days 1, 3, and 5 alter MCA occlusion followed by administration of EPO (1440 IU/day) IV by ALZET® Pump beginning day 7, 8, 9. The first injection was administered 24 hours after stroke-surgery.
Group 8: n=8; hCG (10,000 IU/day) delivered by IM on days 1, 3, and 5 after MCA occlusion followed by administration of EPO (1440 IU/day) IV by ALZET® Pump beginning day 7, 8, 9. The first injection was administered 24 hours after stroke surgery.
Group 9: n=8; hCG (30,000 IU/day) delivered by IM on days 1, 3, and 5 after MCA occlusion followed by administration of EPO (1440 IU/day) IV by ALZET® Pump beginning day 7, 8, 9. The first injection was administered 24 hours after stroke surgery.

As can be seen in FIG. 1, functional improvement for those animals receiving hCG followed by EPO was better than those receiving EPO alone.

Conversion to human administration follows an allometric scaling factor of 8 to convert from mg/kg administered to rats to mg/m² for human administration. Following the guidelines established for this conversion (Guidance for Industry: Estimating the Maximum Safe Starting Does in Initial Clinical Trials for Therapeutics in Adult Healthy Volunteers, U.S. Department of Health and Human Services, FDA Center for Drug Evaluation and Research, July 2005), the observed optimal dose for rats of 300 IU/day converts to:

$$HD=[AD*AK_m]/HK_m$$

Wherein,
HD=Human dose,
AD=Animal dose
$AK_m$=Animal $k_m$ factor
$HK_m$=Human $k_m$ factor Therefore, 300 IU/day (which is equivalent to 30 µg of hCG per day, i.e., 1 µg hCG=10 IU hCG in this study) for an average rat of weight 305 g, is equivalent to 98.4 µg/kg dose in the animal. With a rat $k_m$ factor of 8 and a human $k_m$ factor of 37, the optimal dose of hCG for human administration is therefore calculated as $$HD=98.4 \text{ µg/kg}*8/37=21.28 \text{ µg/kg or } 212.8 \text{ IU/kg day}$$

The human dose of EPO can be calculated, with an activity in the present example of the 1440 IU/day dose of EPO for an average rat of weight 305 g, is equivalent to 4,721.3 IU/kg dose in the animal. With a rat $k_m$ factor of 8 and a human $k_m$ factor of 37, the optimal dose of EPO for human administration is therefore calculated as $$HD=4,721.3 \text{ IU/kg}*8/37=1020.82 \text{ IU/kg}$$

Example 2

Functional Improvement Post-Stroke Using hCG+EPO

A second group of male rats were injured through temporary occlusion of the right middle cerebral artery (MCA) as described in Example 1, following which doses of human derived Human chorionic gonadotropin (hCG) were administered, followed by 3 days of Erythropoietin (EPO, Epogen 1440 IU/day) as described in Example 1.

Male Long Evans rats (280-330 g) were fasted overnight but allowed free access to water. Atropine sulfate (0.5 mg/kg, i.p.) was injected 10 min before anesthesia. Anesthesia was induced with 3.5% isoflurane in a mixture of 70% nitrous oxide and 30% oxygen. All rats were orally intubated and mechanically ventilated. During ventilation, the animals were paralyzed with pancuronium bromide (0.6 mg/kg, i.p.).

Behavioral tests were performed in all rats before MCAo and during occlusion (at 60 min) to confirm, success of the MCAo as described in Example 1.

Treatment and experimental groups were as follows:
Group 1: n=10; Saline solution (of equal volume to hCG administered IM) was administered IM on days 1, 3, and 5, followed by administration of Saline IV by ALZET® Pump beginning day 7, 8, 9 after surgery.
Group 2: n=10; hCG (440 IU/day) was delivered by IM on days 1, 3, and 5 after MCA occlusion followed by administration of EPO (1440 IU/day) IV by ALZET® Pump beginning day 7, 8, 9.
Group 3: n=10; hCG (440 IU/day) was delivered by IM on days 1, 3, and 5 after MCA occlusion followed by administration of Saline at an equivalent rate of volume delivered using IV by ALZET® Pump beginning day 7, 8, 9,
Group 4: n=10; Saline was delivered by IM on days 1, 3, and 5 after MCA occlusion followed by administration of EPO (1440 IU/day) IV by ALZET® Pump beginning day 7, 8, 9.
Group 5: n=5. No MCAo, no treatment; animals were trained and tested in four behavioral tasks at week −1, 1, 2, 3, 4, and 6.

Figure 2:
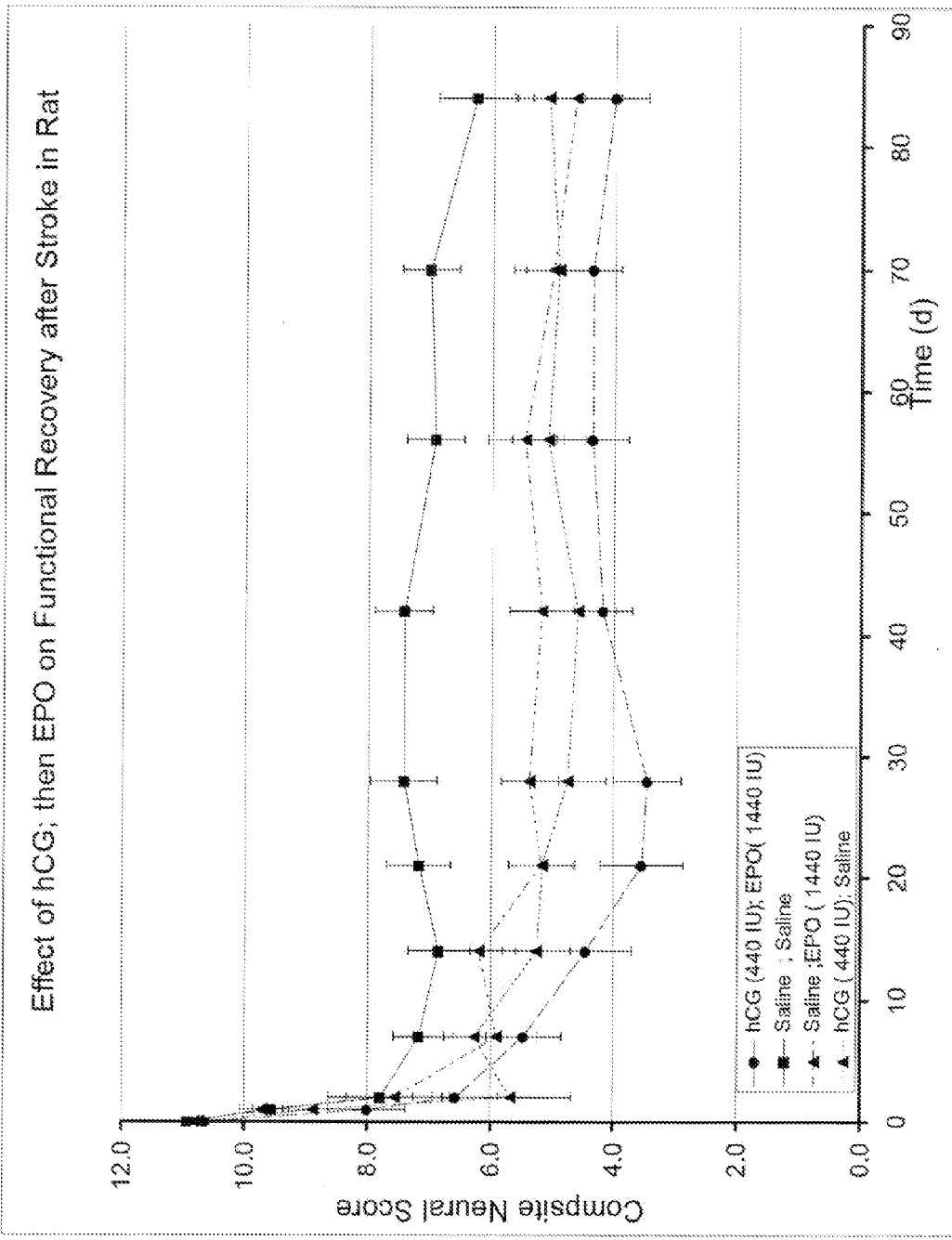
FIG. 2 shows the differential effect on functional recovery of a rat subjected to a MCAo stroke, compared to untreated controls, of 440 IU of hCG with an IV administration of 1440 IU EPO per day, hCG alone, or EPO alone.
Figure 3:
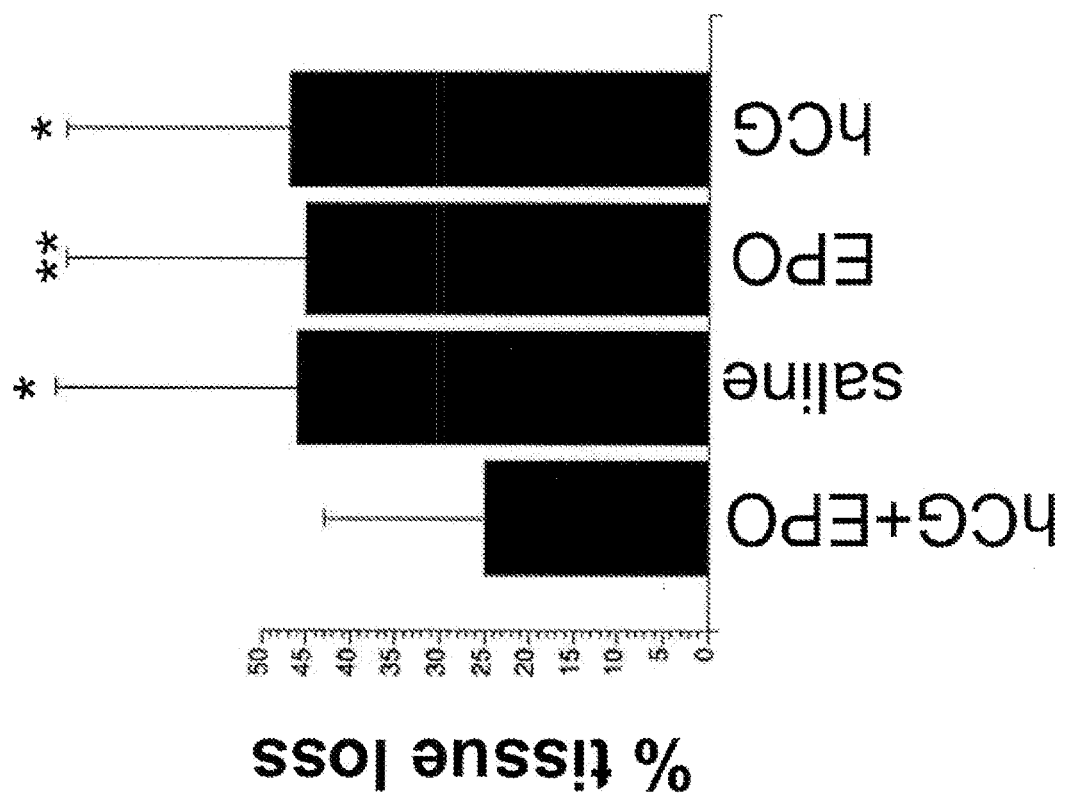
FIG. 3 is a graph indicating % tissue loss (compared to non-stroke hemisphere) in rats subjected to a MCAo stroke, compared to untreated controls, of 440 IU of hCG with an IV administration of 1440 IU EPO per day, hCG alone, or EPO alone.
Figure 4:
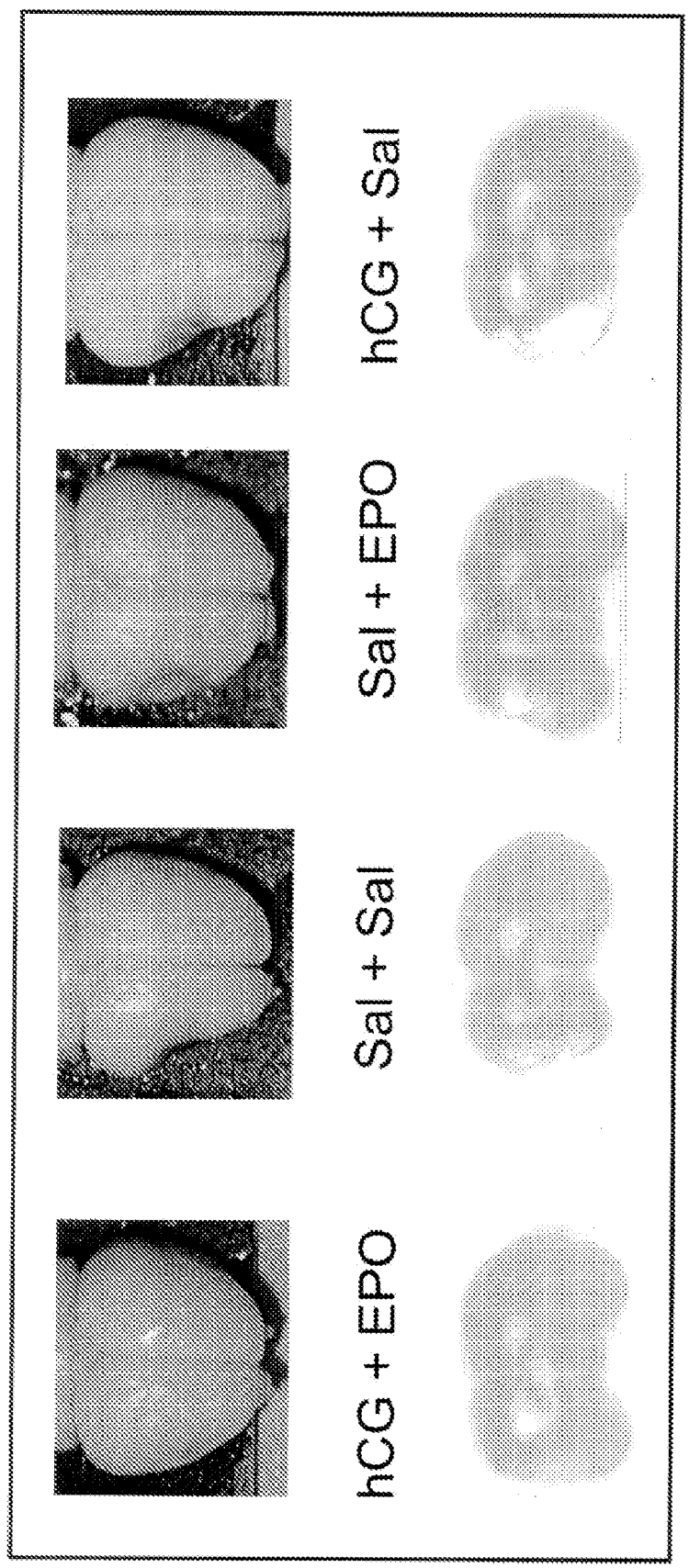
FIG. 4 shows representative images of tissue loss in rats subjected to a MCAo stroke, compared to untreated controls, of 440 IU of hCG with an IV administration of 1440 IU EPO per day, hCG alone, or EPO alone.

FIG. 2 shows the difference in neurological function, as graded on a scale of 0-12, between the test groups at the same time point post-stroke. As can be seen, there is a marked functional improvement arising from administration of hCG followed by EPO in the manner described herein. Further, FIG. 3 shows a graph indicating the % tissue loss (as compared to non-stroke hemisphere) for these test groups, and FIG. 4 shows images representative of the tissue loss for each group.

Figure 5:
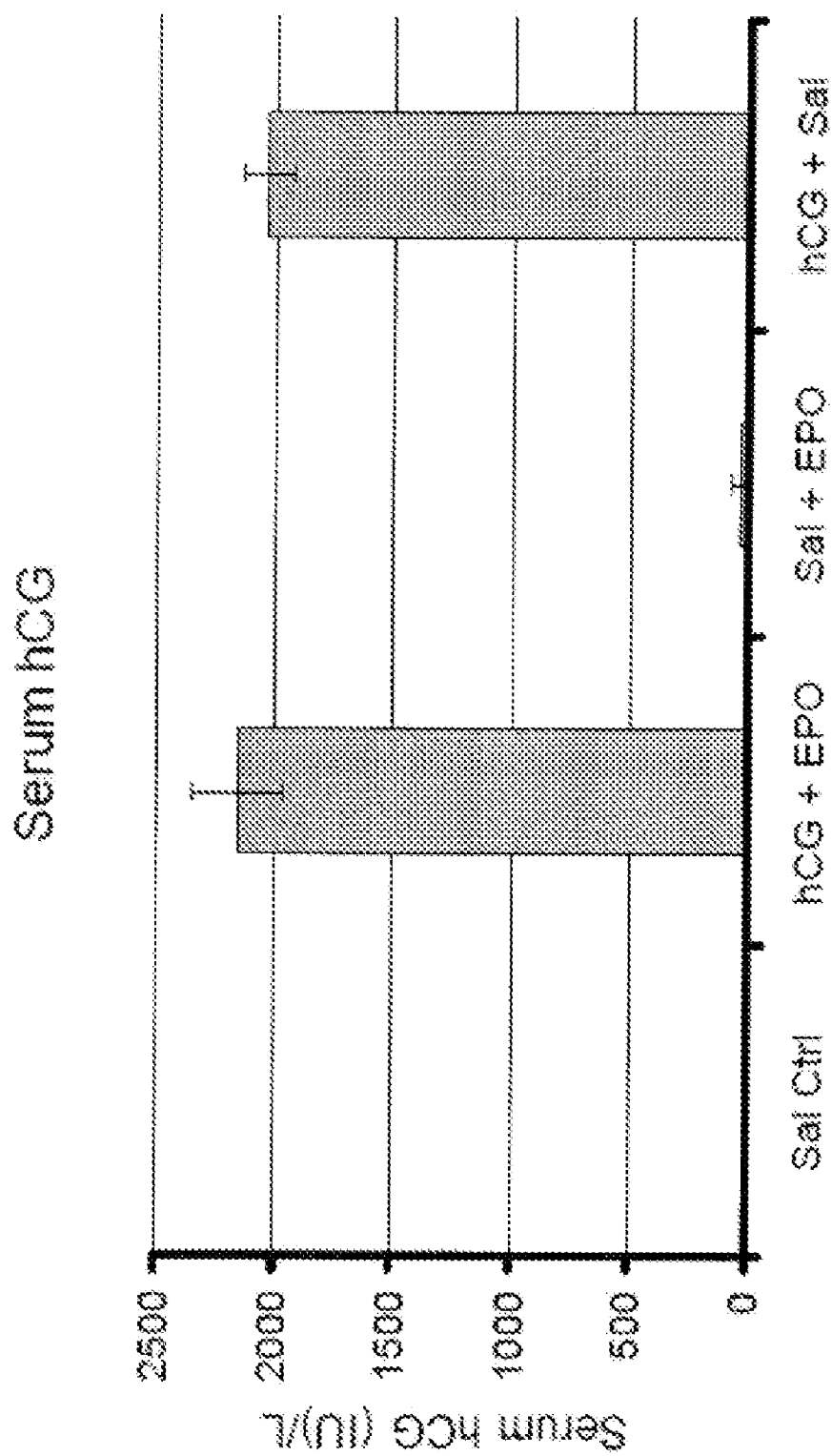
FIG. 5 is a bar graph indicating serum hCG levels as measured after a third IM administration of hCG in Example 2.

Additionally, serum hCG levels were measured after the third IM administration of hCG. As shown in FIG. 5, circulating hCG levels were significant in dosed animals.

Example 3

Using hCG+ EPO in the Treatment of Acute Stroke in Humans

A study has begun in human stroke patients that will involve providing a patient with 3 once-daily IM doses of hCG (at 10,000 IU/dose) on days 1, 3, and 5 of study participation, followed by a one day wash, out period (day 6), followed by three once-daily I.V. doses of erythropoietin (at 30,000 IU/dose) on days 7, 8, and 9 of study participation. The first IM hCG dose is targeted to be delivered between 24 and 48 hours after a moderate-severe stroke event. Patients will be examined at several points during treatment, as well as 6 weeks and 3 months after stroke onset. Baseline assessments will include clinical/safety, neurological, hematological, and vascular status, as well as a brain MRI. Assessments of clinical/safety, neurological, hematological, and vascular status will be repeated at 1 day, 15 days, and 80 days after completing the treatment. A brain MRI will be repeated 80 days after completing the treatment (which will be approximately 90 days after stroke onset) for comparison purposes.

Example 4

Administration of Prolactin

Male rats (250-300 g) were used in two prolactin dosing experiments. Prolactin was given by subcutaneous mini-osmotic pump infusions (ALZET® minipumps)—one injection daily. Stock prolactin was diluted in bicarbonate buffer and the stock was further diluted in 1 mg/ml Rat Serum Albumin (RSA) in saline for injections. The rats did not receive ischemic injuries. On the $6^{th}$ day the animals received 6 BrdU injections (Sigma-Aldrich) (60 mg/kg, i.p.) over 10 hrs and were sacrificed 30 min following the final BrdU injection. The brains were cryosectioned and BrdU+ cells were quantified in the SVZ using 8 sections per animal. The results are presented as total number of BrdU+ cells in the SVZ or as an average per section as indicated in the figure legend.

Figure 6:
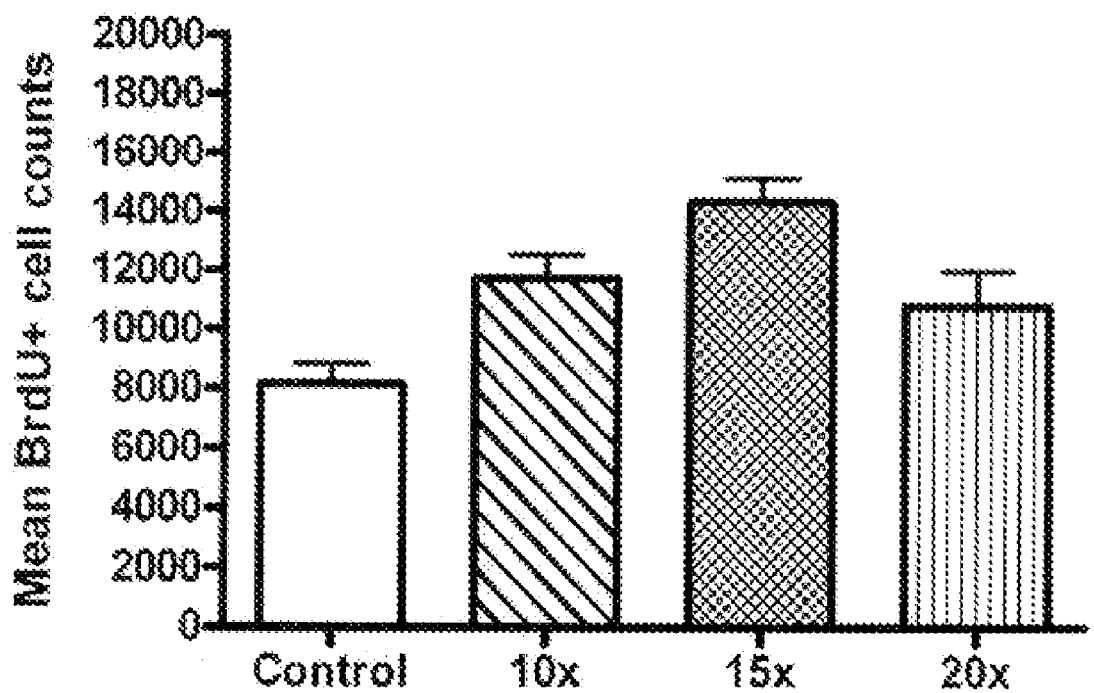
FIG. 6 shows the result of six day subcutaneous prolactin infusions in male rats at 10, 15, and 20 times the concentrations used for intracerebroventricular infusions. The total number of bromodeoxyuridine positive (BrdU+) cells in the sub-ventricular zone (SVZ) for 8 sections from each animal is presented. The greatest increase in SVZ proliferation levels was observed with the 15 times dose (170 µg/day for 6 days). (10 times=113 µg/day; 20 times=226 µg/day; Control=rat serum albumin only (RSA)). Significance relative to control: 10×=*p<0.05; 15×=**p<0.01; 20×=p<0.05; n=3 for all conditions; one way analysis of variance (ANOVA) with Tukey posthoc test.

Experiment #1:
Rats were dosed for 6 days and received subcutaneous infusions of RSA (control) or rat prolactin (National Hormone and Peptide Program, Torrance, Calif.) at the following doses (3 rats in each group):
*10×=99 ul/pump (2 mg/0.25 ml PRL)—113 µg/day
**15×=148.5 ul/pump (2 mg/0.25 ml PRL)—170 µg/day
***20×=198 ul/pump (2 mg/0.25 ml PRL)—226 µg/day
wherein
*10×=10 times the dose given for intracerebroventricular infusions (approx 11 µg/day).
**15×=15 times the dose given for intracerebroventricular infusions.
***20×=20 times the dose given for intracerebroventricular infusions.
Results:
As shown in FIG. 6, 170 µg/day resulted in the largest increase in proliferation (number of BrdU+ cells) within the forebrain SVZ.

Figure 7:
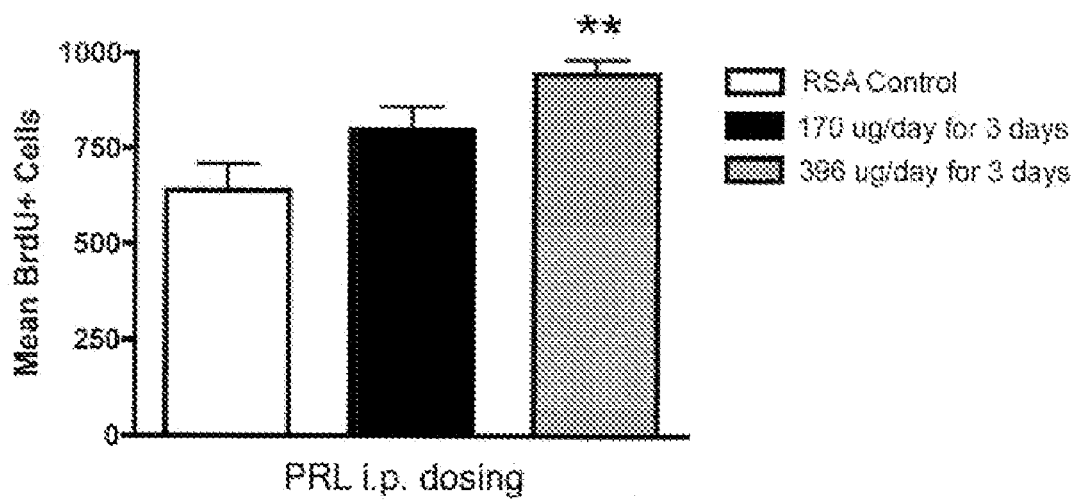
FIG. 7 shows the results of prolactin dosing in male rats using single daily intraperitoneal injections. The total number of BrdU+ cells per section are presented for each dosing regime. (A) A small increase in SVZ proliferation was observed with high 3 day doses. (B) The most robust dosing condition for increasing SVZ proliferation levels used a low, 170 µg/day dose each day over 6 days. Significance is relative to RSA control, n=3; *p<0.05; **p<0.01; one-way ANOVA followed by a Tukey posthoc test.
Figure 7:
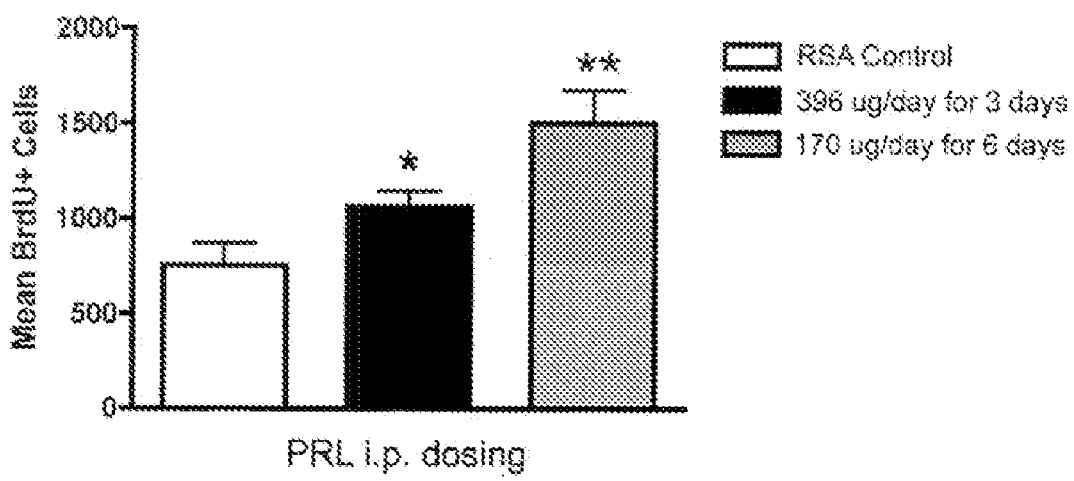

Experiment #2:
Rats were dosed for 3 or 6 days and received daily single intraperitoneal injections of RSA or rat prolactin (National Hormone and Peptide Program, Torrance, Calif.) at the following doses (3 rats in each group):
170 µg/day for 3 days
396 µg/day for 3 days
170 µg/day for 6 days
Results:
As shown in FIG. 7, 170 µg/day delivered for 6 days resulted in the largest increase in proliferation (number of BrdU+ cells) within the forebrain SVZ.

Example 5

Administration of hCG

The purpose of this study is to determine the dose of hCG that maximizes cell proliferation in the forebrain germinal zone and tissue regeneration of adult male rats that have received a pial-strip devasculaizing ischemic injury to the motor cortex.

Methods

Animals and Surgery 250-300 g male rats received a pial-strip devascularization ischemic injury to the motor cortex as previously described (Gonzalez and Kolb. A comparison of different models of stroke on behaviour and brain morphology. Eur J Neurosci. 2003. 18(7): 1950-1962). With the animals under sodium pentobarbital anesthesia (60 mg/kg), a rectangular hole was drilled into the frontal and parietal bones running from +4 to −2 mm anterior/posterior to the bregma and running laterally from 1.5 to 4.5 mm from midline. The dura was removed and a sterile saline-soaked cotton swab was used to wipe the pia and attached blood vessels from the cortical surface.

Dosing

Beginning one day post-stroke (24 hrs later), animals received a single intramuscular (i.m.) injection of hCG (National Peptide and Hormone Program, Torrance, Calif.)). Doses were given as described in Table 1 and were delivered in either three injections over 5 days (dosed on days 1, 3, and 5) or as daily injections over one week and injections were given at 9:00 am each day. Control rats received injections of rat serum albumin in saline (RSA; Sigma, 1 mg/ml). On the day of the final dose animals received 6 BrdU injections over 10 hrs, beginning 30 min after the hCG injection. BrdU (Sigma-Aldrich) was given at a dose of 60 mg/kg, i.p. Animals were transcardially perfused with 4% paraformaldehyde. Brains were dissected, cryoprotected in sucrose and cryosectioned. Brains were cryosectioned at 14 microns in two series of 8 slides each with 8 sections per slide. Immunostaining was performed using rabbit anti-phosphohistone H3 (anti-pHH3; 1:100; Upstate Biotechnologies), Rat anti-BrdU (1:100; Seralab), goat, anti-doublecortin (DCX; 1:100; Santa Cruz Biotechnologies). The number of phosphohistone H3 (pHH3—a marker of mitotically-active cells), BrdU, and doublecortin (DCX—a marker of immature neurons) positive cells in the forebrain subventricular zone (SVZ) around the lateral ventricle of each animal was quantified in 8 sections and presented as the average number of positive cells per lateral ventricle.

Statistics

Values are means+standard error of the mean (SEM). Significance was determined using a one-way ANOVA followed by a Tukey HSD posthoc test (*$p<0.05$; **$p<0.01$). Three animals were included in each group.

Results

The present study examines the ability of intramuscular injections of hCG to promote the proliferation of neural stem cells and progenitor cells residing in the adult forebrain subventricular zone (SVZ) following stroke. Animals underwent pial strip devascularization surgery to induce a focal ischemic injury in the motor cortex and treatments began 24 hrs later. In a high bolus dose strategy, animals received 3 doses of hCG over five days on days 1 (24 hrs post-stroke), 3 and 5 as summarized in Table 1. Animals were sacrificed on day 5 for analysis of the levels of proliferation in the forebrain SVZ. As shown in Table 2 and FIG. 8, this regime was effective in increasing proliferation compared to stroked animals receiving RSA control injections. At a dose of 1000 µg, proliferation was increased by almost 2.5 fold and, as shown in FIG. 9, the number of newly generated doublecortin positive (DCX+) neurons in the SVZ of these animals was similarly significantly increased.

Figure 10:
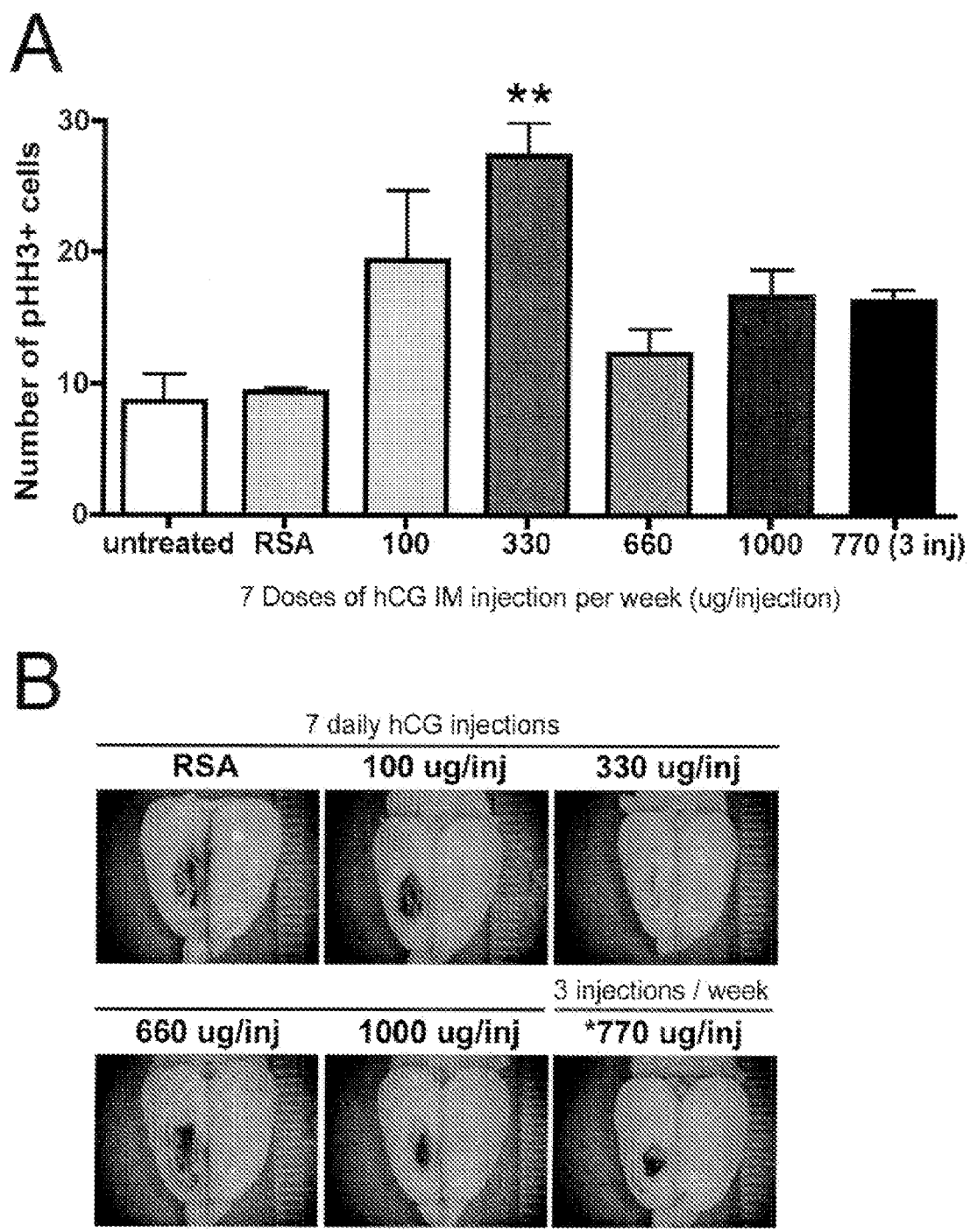
FIG. 10 shows the results of single intramuscular injections of hCG given daily for 7 days starting 24 hrs post-stroke (stroke=day 0), (A) The daily 330 μg/injection dosing regime significantly increased the number of proliferating (pHH3+ cells) in the SVZ relative to all other dosing conditions and controls (n=3; *p<0.01; one way ANOVA with Tukey posthoc). (B) Observation of the ischemic lesions in the motor cortex of dosed rats revealed that animals receiving the 330 μg/injection daily dosing regime demonstrated new tissue growth and filling in of the lesion site with a tissue plug.
Figure 11:
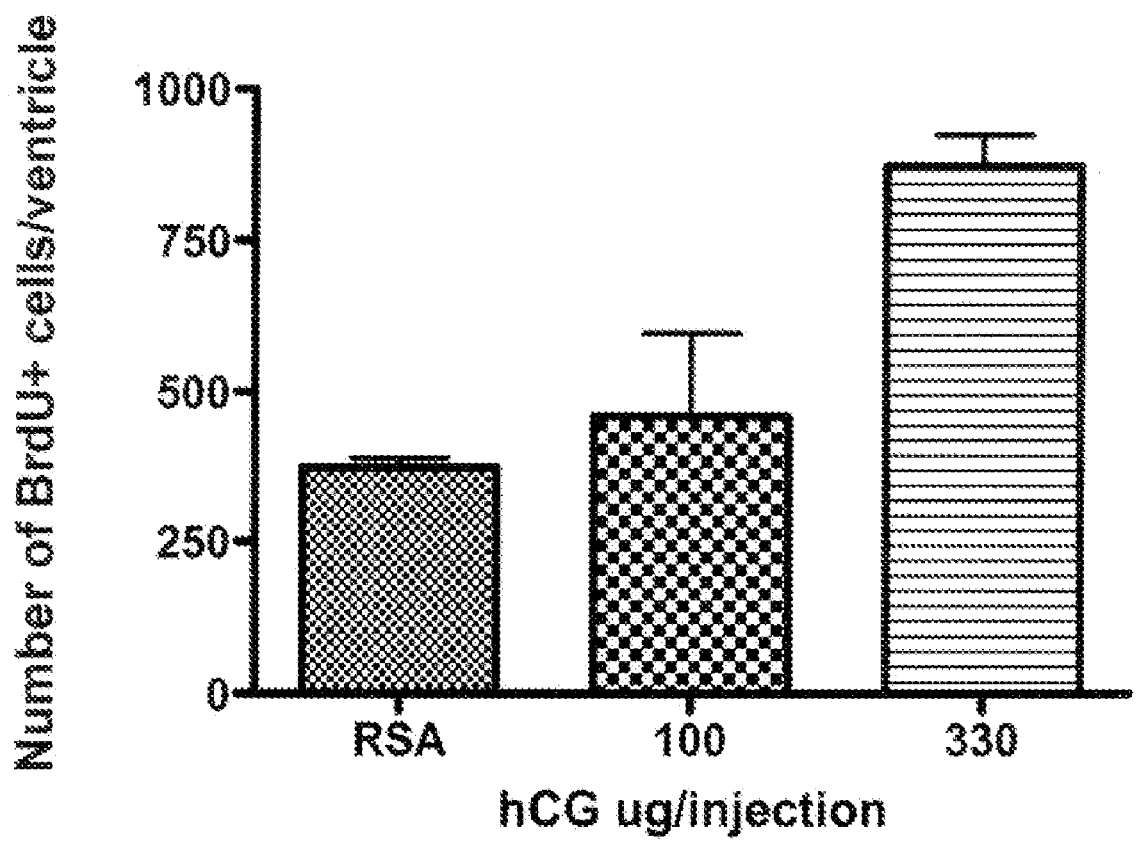
FIG. 11 shows increased proliferation in the SVZ of 330 μg/injection daily hCG dosed animals as confirmed by counts of BrdU+ cells. The number of BrdU+ cells per ventricle was significantly increased in the 330 μg/injection condition relative to control and 100 μg/injection (p<0.01; n=3; one way ANOVA with Tukey posthoc analysis). These results farther confirmed the increase in proliferation observed with pHH3 staining.

In another study, animals received daily dosing with hCG as summarized in Table 1 for 7 days, beginning 24 hrs post-stroke, and the animals were given BrdU on day 7 for 10 hrs and then sacrificed. As shown in FIG. 10A, the number of dividing cells in the SVZ, as indicated by pHH3 immunoreactivity, was significantly increased in the 330 µg/injection group relative to all other groups. This increase was confirmed by quantifying the number of BrdU+ cells in the SVZ of these animals relative to RSA controls (FIG. 11). There was a trend level increase in the 100 µg treatment group relative to pial strip RSA controls (FIGS. 10A and 11). Note that the untreated animals in FIG. 10 received no injections and no pial strip stroke. As an internal control, a group received the same total dose as the 330 µg/injection group (see Table 1), but the hCG was given in 3 injections of 770 µg/injection on days 1, 3 and 5 and the animals were sacrificed on day 5. Based on this study, a low, regular dose of hCG given at 330 µg/injection daily was most effective for increasing proliferation in the forebrain SVZ following ischemic damage in the brain.

To determine whether any of the dosing regimes might result in the growth of new cortical tissue we analyzed the lesion site in cortex of hCG treated animals. Tissue regrowth was particularly evident in the low, regular daily dosing regime the 330 µg/injection dosed group of animals (FIG. 10B).

Any patents or publications mentioned in the specification are indicative of the level of those skilled in the art to which the invention pertains. These patents and publications are herein incorporated by reference in their entirety to the same extent as if each individual publication was specifically and individually indicated to be incorporated by reference.

The present invention is not limited in scope by the embodiments disclosed in the examples which are intended as illustrations of a few aspects of the invention and any embodiments which are functionally equivalent are within the scope of this invention. Various modifications of the methods and kits in addition to those shown and described herein will become apparent to those skilled in the art and are intended to fall within the scope of the appended claims. Further, while only certain representative combinations of the compositions disclosed herein are specifically discussed in the embodiments above, other combinations of the compositions will become apparent to those skilled in the art and also are intended to fall within the scope of the appended claims. Thus a combination of steps or compositions may be explicitly mentioned herein; however, other combinations of steps or compositions are included, even though not explicitly stated

TABLE 1 hCG Dosing Strategy. Rats received either three intramuscular (I.M.) injections of hCG over 5 days or daily injections or 7 days beginning 24 hrs post-stroke. Control rats received injections of RSA only.

Figure 8:
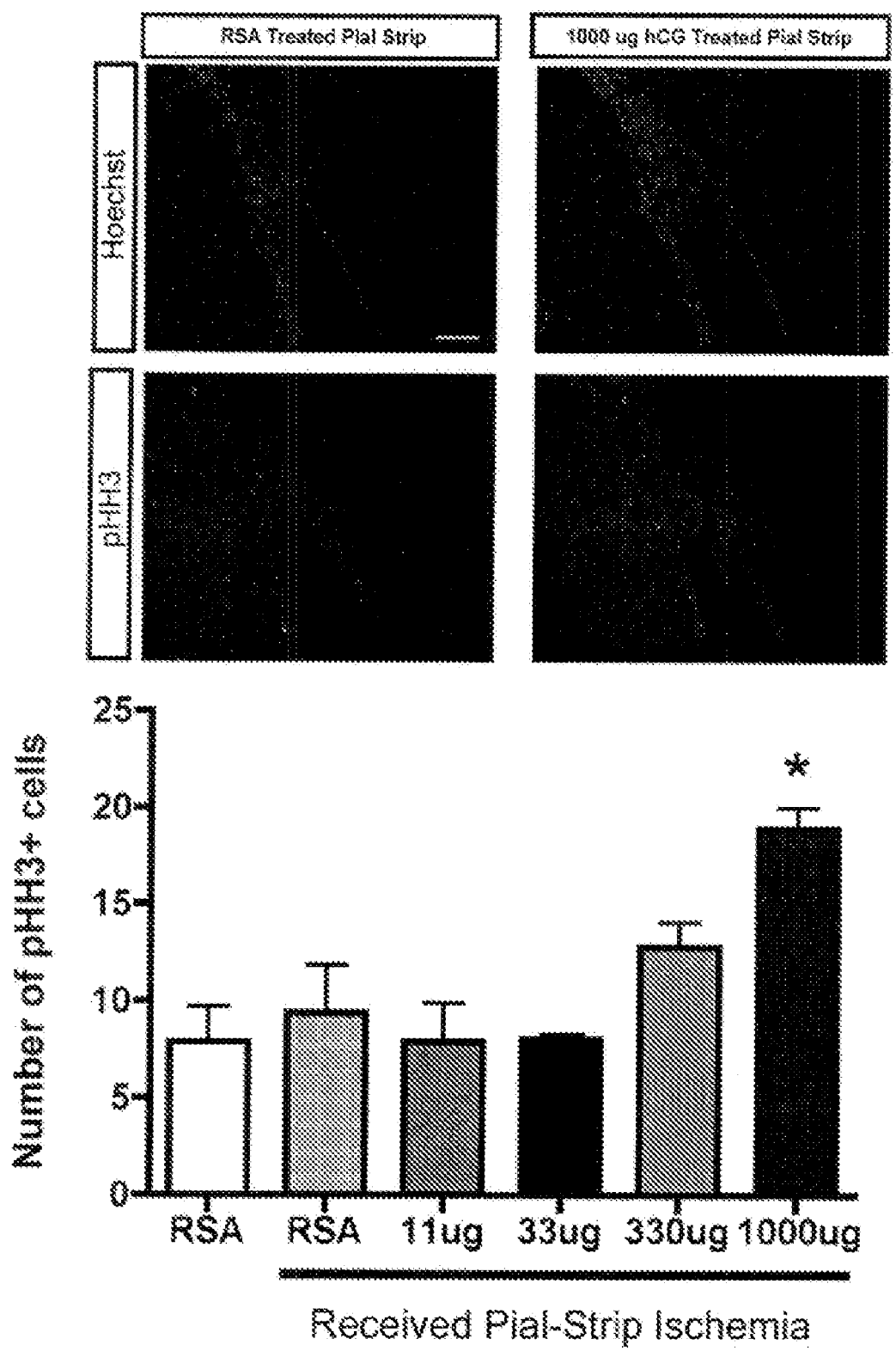
FIG. 8 shows that single intramuscular injections of hCG on days 1, 3, and 5 post-stroke (stroke=day 0) trigger significantly increased proliferation in the forebrain SVZ. Significant increases in the number of Phospho-Histone H3 positive (pHH3+) cells per ventricle were observed in the 1000 μg dose condition (n=3; *p<0.05; one way ANOVA with Tukey posthoc). Images show the nuclear label. Hoechst and pHH3 expression in the dorsolateral corner of the lateral ventricles in RSA pial strip control rats versus 1000 μg hCG dosed animals, note the increase in total cell number and pHH3 expression in SVZ of 1000 μg dosed animals.
Figure 9:
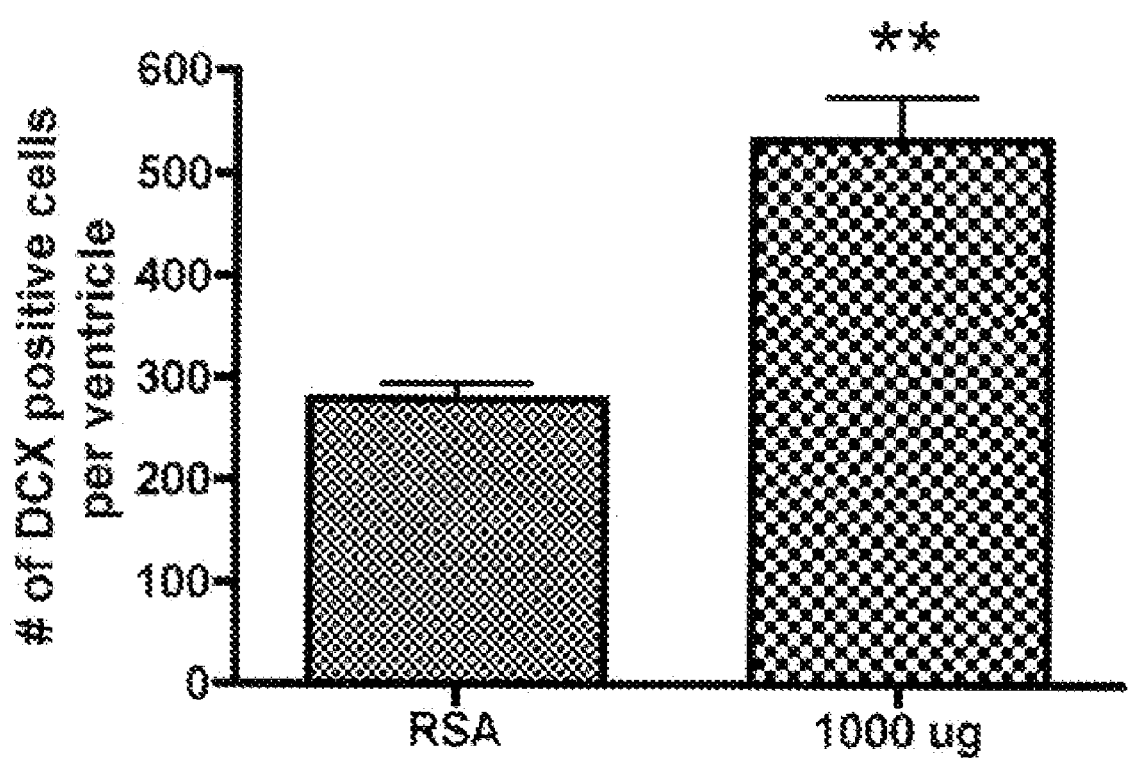
FIG. 9 shows that single intramuscular injections of 1000 μg per day of hCG on days 1, 3, and 5 post-stroke (stroke=day 0) trigger increased neurogenesis in the forebrain SVZ. The number of doublecortin+ neurons was quantified in the dosed animals and was doubled in the 1000 μg dose animals, (n=3; **p<0.01).

| Total Dose (IUs hCG) | Dose/injection (IUs hCG) | Dose/injection (micrograms (µg) hCG) |
|---|---|---|
| FIGS. 8 and 9 | | |
| Dosed on days 1, 3, and 5 | | |
| RSA (no stroke) | | |
| RSA | | |
| 330 | 110 | 11 |
| 990 | 330 | 33 |
| 9900 | 3300 | 330 |
| 30000 | 10000 | 1000 |
| FIGS. 10 and 11 | | |
| Dosed daily for 7 days | | |
| Untreated (no stroke and no injections) | | |

TABLE 1-continued hCG Dosing Strategy. Rats received either three intramuscular (I.M.) injections of hCG over 5 days or daily injections or 7 days beginning 24 hrs post-stroke. Control rats received injections of RSA only.

| Total Dose (IUs hCG) | Dose/injection (IUs hCG) | Dose/injection (micrograms (μg) hCG) |
|---|---|---|
| RSA | | |
| 7000 | 1000 | 100 |
| 23100 | 3300 | 330 |
| 46200 | 6600 | 660 |
| 70000 | 10000 | 1000 |
| Dosed on days 1, 3, and 5 | | |
| 23100 | 7700 | 770 |

TABLE 2

Actual values ± SEM presented as the average number of positive cells per lateral ventricle for quantification of pHH3+, BrdU+ and DCX+ cells in animals dosed with hCG 24 hrs following pial strip devascularizing stroke relative to controls.

| Dosing Condition (μg/injection) Daily Dosing for 1 Week | pHH3+ Cells Number of Positive Cells per Ventricle | BrdU+ Cells |
|---|---|---|
| Untreated No Stroke | 8.7 ± 2 | — |
| RSA | 9.3 ± 0.3 | 374 ± 15 |
| 10 | 19.3 ± 5 | 459 ± 138 |
| 330 | 27 ± 3** | 874 ± 91* |
| 660 | 12.3 ± 2 | — |
| 1000 | 17 ± 2 | — |
| 770 (dosed on days 1, 3 and 5) | 16 ± 1 | — |
| 5 Day Dosing with Injections on Days 1, 3 and 5 | | DCX+ Cells |
| RSA | 8.7 ± 1 | 280 ± 15 |
| 11 | 8 ± 2 | — |
| 33 | 8 ± 0.1 | — |
| 330 | 13 ± 1 | — |
| 1000 | 19 ± 1* | 533 ± 42* |

What is claimed is:

1. A method of treating or ameliorating a neurodegenerative disease or condition in a mammal comprising administering to the mammal an effective amount of human chorionic gonadotropin (hCG) during a first treatment period lasting at least three days and administering to the mammal an effective amount of erythropoietin (EPO) during a second treatment period lasting at least three days, wherein the neurodegenerative disease or condition is a stroke, and wherein the second treatment period starts after the end of the first treatment period.

2. The method of claim 1, wherein the hCG is administered systemically.

* * * * *